United States Patent
Chu

(10) Patent No.: US 8,500,624 B2
(45) Date of Patent: Aug. 6, 2013

(54) SYSTEMS AND METHODS FOR SLING DELIVERY AND PLACEMENT

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 913 days.

(21) Appl. No.: 10/973,010

(22) Filed: Oct. 25, 2004

(65) Prior Publication Data

US 2006/0089524 A1 Apr. 27, 2006

(51) Int. Cl.
*A61F 2/00* (2006.01)

(52) U.S. Cl.
USPC ............................................................ 600/29

(58) Field of Classification Search
USPC ....... 600/29–32, 37; 128/898–899; 606/151, 606/190
See application file for complete search history.

(56) References Cited

U.S. PATENT DOCUMENTS

| | | | |
|---|---|---|---|
| 4,798,193 A | 1/1989 | Giesy et al. | |
| 4,824,435 A | 4/1989 | Giesy et al. | |
| 5,337,736 A | 8/1994 | Reddy | |
| 5,439,467 A | 8/1995 | Benderev et al. | |
| 5,500,000 A | 3/1996 | Feagin et al. | |
| 5,582,188 A | 12/1996 | Benderev et al. | |
| 5,766,221 A | 6/1998 | Benderev et al. | |
| 5,899,909 A | 5/1999 | Claren et al. | |
| 6,042,534 A | 3/2000 | Gellman et al. | |
| 6,042,536 A | 3/2000 | Tihon et al. | |
| 6,110,101 A | 8/2000 | Tihon et al. | |
| 6,273,852 B1 | 8/2001 | Lehe et al. | |
| 6,406,423 B1 | 6/2002 | Scetbon | |
| 6,423,080 B1 | 7/2002 | Gellman et al. | |
| 6,475,139 B1 | 11/2002 | Miller | |
| 6,494,887 B1 | 12/2002 | Kaladelfos | |
| 6,592,515 B2 | 7/2003 | Thierfelder et al. | |
| 6,612,977 B2 | 9/2003 | Staskin et al. | |
| 6,641,524 B2 | 11/2003 | Kovac | |
| 6,648,921 B2 | 11/2003 | Anderson et al. | |
| 6,652,450 B2 | 11/2003 | Neisz et al. | |
| 6,666,817 B2 | 12/2003 | Li | |
| 6,685,629 B2 | 2/2004 | Therin | |
| 6,802,807 B2 * | 10/2004 | Anderson et al. | 600/29 |
| 6,911,003 B2 | 6/2005 | Anderson et al. | |
| 6,936,052 B2 | 8/2005 | Gellman et al. | |
| 2002/0099258 A1 | 7/2002 | Staskin et al. | |
| 2002/0128670 A1 | 9/2002 | Ulmsten et al. | |
| 2003/0004395 A1 | 1/2003 | Therin | |
| 2003/0009181 A1 | 1/2003 | Gellman et al. | |
| 2003/0023138 A1 | 1/2003 | Luscombe | |
| 2003/0176875 A1 * | 9/2003 | Anderson et al. | 606/151 |
| 2003/0225424 A1 | 12/2003 | Benderev | |
| 2004/0039246 A1 | 2/2004 | Gellman et al. | |
| 2004/0073234 A1 | 4/2004 | Chu et al. | |
| 2004/0087970 A1 | 5/2004 | Chu et al. | |
| 2004/0106846 A1 | 6/2004 | Gellman | |
| 2004/0116944 A1 | 6/2004 | Chu et al. | |

(Continued)

FOREIGN PATENT DOCUMENTS

| | | |
|---|---|---|
| GB | 2353220 | 10/2000 |
| WO | WO-98/35616 | 8/1998 |

(Continued)

*Primary Examiner* — Christine Matthews

(57) ABSTRACT

The present invention provides devices and methods for delivering an implantable sling to an anatomical location in a patient.

2 Claims, 16 Drawing Sheets

(56) References Cited

U.S. PATENT DOCUMENTS

| | | |
|---|---|---|
| 2004/0122474 A1 | 6/2004 | Gellman et al. |
| 2004/0133217 A1 | 7/2004 | Watschke |
| 2004/0225181 A1 | 11/2004 | Chu et al. |
| 2004/0230206 A1 | 11/2004 | Gellman et al. |
| 2004/0243166 A1 | 12/2004 | Odermatt et al. |
| 2005/0021086 A1 | 1/2005 | De Leval |
| 2005/0027368 A1 | 2/2005 | Hellhammer et al. |
| 2005/0038451 A1 | 2/2005 | Rao et al. |
| 2006/0009673 A1* | 1/2006 | Chan .............................. 600/29 |
| 2006/0106277 A1* | 5/2006 | Romero Maroto ............. 600/37 |

FOREIGN PATENT DOCUMENTS

| | | |
|---|---|---|
| WO | WO-99/37216 | 7/1999 |
| WO | WO 01/30246 | 5/2001 |
| WO | WO 02/30293 | 4/2002 |
| WO | WO-02/062237 | 8/2002 |
| WO | WO 2004/086983 | 10/2004 |

\* cited by examiner

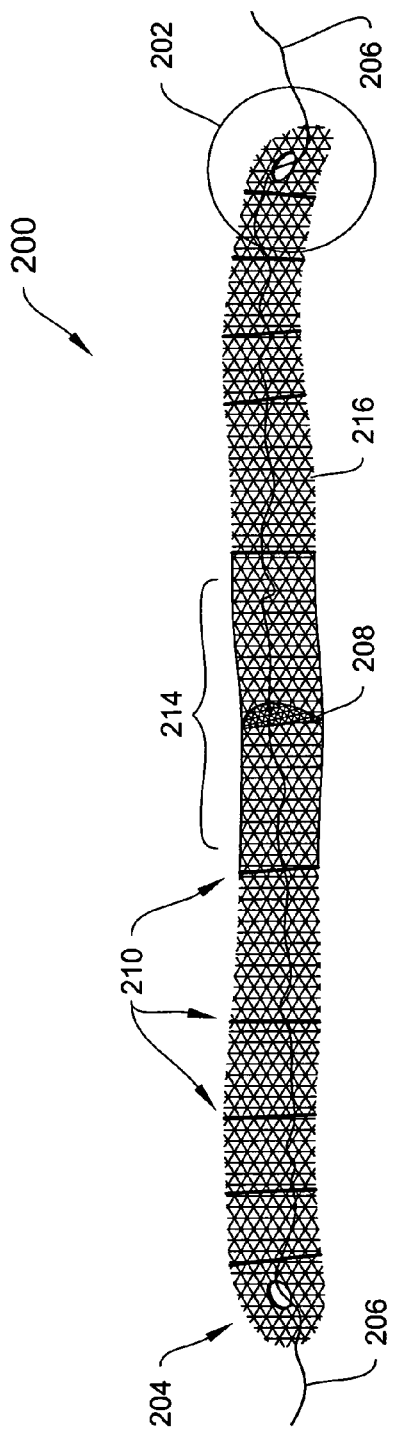
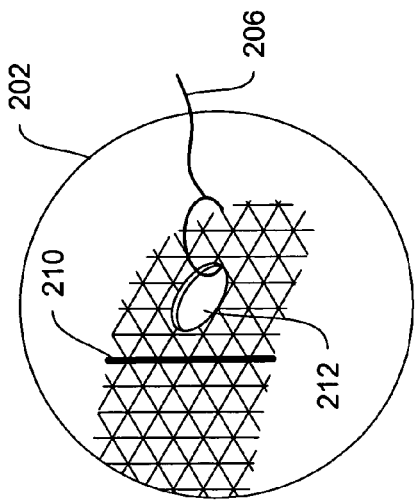
FIGURE 2A
FIGURE 2B

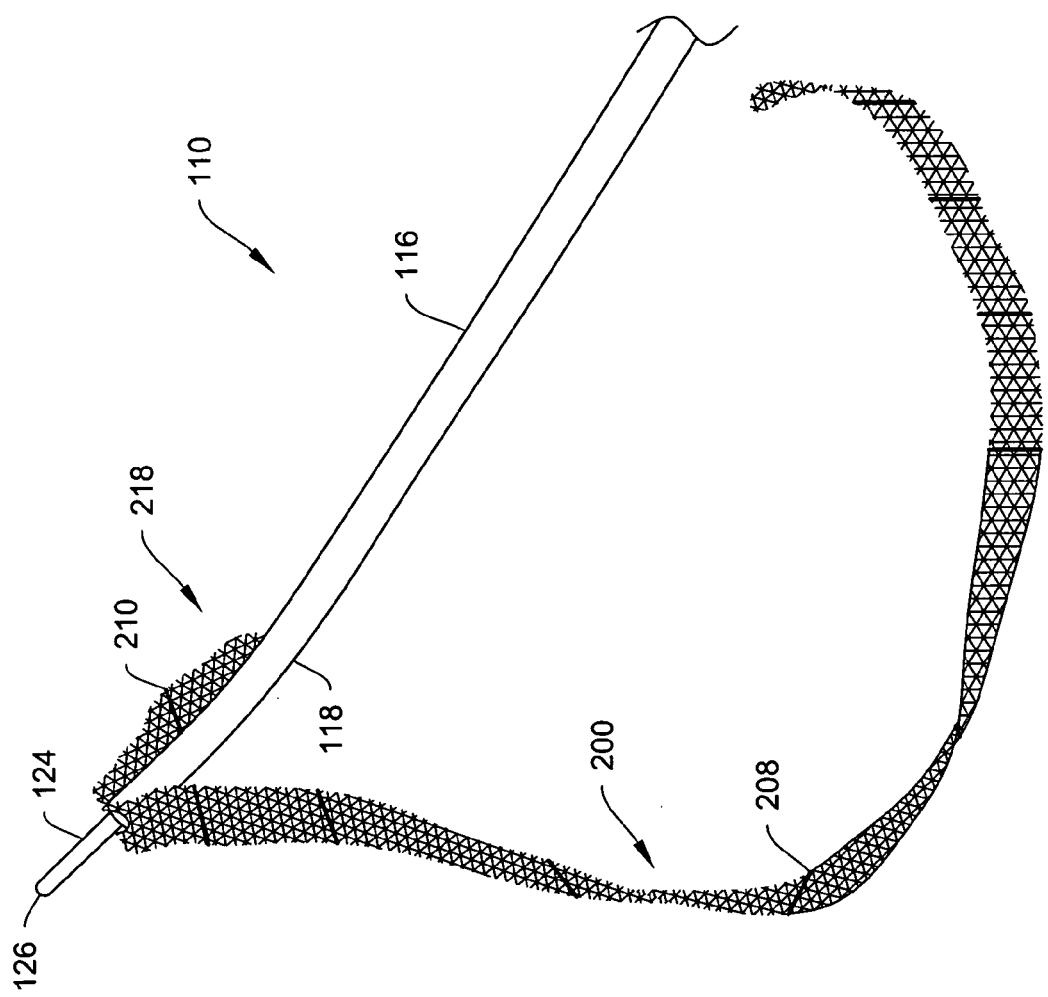

SYSTEMS AND METHODS FOR SLING DELIVERY AND PLACEMENT

FIELD OF THE INVENTION

The invention generally relates to systems and methods for delivering a medical implant to an anatomical location in a patient. More particularly, in various embodiments, the invention relates to systems and methods for delivering a supportive sling to the periurethral tissue of a patient to provide urethral support.

BACKGROUND OF THE INVENTION

Stress urinary incontinence (SUI) affects primarily women, but also men, and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow.

A popular treatment of SUI uses a surgical sling placed under the bladder neck or the mid-urethra to provide a urethral platform. Placement of the sling limits the endopelvis fascia drop. The sling is traditionally affixed using a bone anchoring method. Recent advances in surgical techniques have demonstrated the effectiveness of anchorless approaches toward mid-urethra sling stabilization. However, conventional anchorless techniques suffer from some deficiencies. For example, some require abdominal incisions, while others require ishiopubic incisions. Additionally, others make it difficult to accurately place the sling at a desired anatomical location.

Accordingly, there is a need for an improved approach to sling placement that simplifies the procedure and reduces trauma to the patient.

SUMMARY OF THE INVENTION

The systems and methods described herein are generally directed to the delivery and application of an implant to an anatomical site in a patient. More particularly, in various embodiments, the invention provides systems and methods for delivering a supportive sling to the periurethral tissue of a patient, without the need for abdominal or ishiopubic incisions. According to a further embodiments, the invention makes it easier for a medical operator to accurately place the supportive sling at a desired anatomical location. In other embodiments, the invention makes it easier for a medical operator to disassociate a sling from a delivery device and/or a remaining portion of a sling assembly.

In one aspect, the invention provides a sling delivery system including a shaft and a handle attached to a proximal end of the shaft. The shaft may be substantially straight or may include one or more curved sections. Additionally, the shaft may lie substantially in one plane or may be shaped to lie in multiple planes. The shaft may be of substantially constant outside diameter or may include portions of differing outside diameters. In various embodiments, the shaft may include hooked and/or helical portions.

Preferably, the system includes a feature located near a distal end of the shaft for impeding a sling assembly from sliding proximally along a substantial portion of the length of the shaft. In one embodiment, the feature includes a tapered distal portion sized and shaped to slidably interfit with a sling assembly, and to inhibit the sling assembly from sliding proximally along a substantial portion of the length of the shaft. According to another embodiment, the feature includes a shoulder extending radially outward near the distal end of the shaft. In one configuration, the shoulder extends around the entire circumference of the shaft. In other configurations, the shoulder extends around only a portion of the circumference. In both cases, the shoulder extends far enough to impede the sling assembly from sliding proximally along a substantial portion of the length of the shaft. According to one embodiment, the feature for impeding proximal movement of the sling assembly along the shaft is formed at a distal portion of the shaft.

In an alternative embodiment, the sling delivery system includes a pusher assembly slidably interfitted over the shaft and slidably actuatable in a distal direction by a medical operator to push an end of a sling assembly off the distal end of the shaft. In one configuration of this embodiment, a distal end of the pusher assembly forms the shoulder for impeding the sling assembly from sliding proximally along the substantial portion of the length of the shaft.

According to another aspect, the invention provides an implantable sling, either alone or as part of a sling delivery system. According to one configuration, the sling or a sling assembly including the sling includes features for indicating length measurements for aiding in positioning of the sling. According to one configuration, the sling and/or sling assembly also includes a feature for indicating a center location along the length of the sling, also for aiding in accurate sling placement. Preferably, the center feature, and the length measurement and/or position-indicating features are distinguishable from each other. By way of example, the length measurement and/or position-indicating features, and center features may be differently colored and/or of different widths.

According to one embodiment, an end of the sling and/or sling assembly may be folded lengthwise toward the center of the sling and/or sling assembly along one of the length indicating features to adjust the effective length of the sling. According to another embodiment, a distal end of a delivery device may slidably engage with the sling and/or sling assembly at an end formed at the fold of the length indicating feature. In one configuration, the distal end of the delivery device engages with a double layer of sling material formed from folding the sling end lengthwise along the length indicating feature and toward the center indicating feature. In another configuration, the sling assembly includes preformed, structurally reinforced through apertures at its ends for slidably engaging with the distal end of the delivery device(s). According to another configuration, the sling assembly includes dilator tubes located at the sling assembly ends for slidably engaging with the distal end of the delivery device(s). In some configurations, the dilator tubes attach directly to the sling ends, whereas in other configurations, the dilator tubes attach to a sleeve in which the sling resides, but does not attach to anything.

According to another aspect, the invention provides a method for delivering a sling to an anatomical location in a patient including the steps of inserting a distal end of a delivery device into a sling assembly end, inhibiting the sling assembly end from sliding proximally along a substantial length of the delivery device, introducing the distal end of the delivery device and the sling assembly end into the body of the patient, and removing the distal end of the delivery device from the sling assembly to deliver the sling to the anatomical location in the patient. According to one embodiment, the step of inserting includes inserting the distal end of the delivery device into the sling assembly at a length indicating feature. According to a further embodiment, the method includes the step of folding an end of a sling included in the sling assembly lengthwise at a length indicating feature to adjust the length of the sling, and the step of inserting includes inserting the distal end of the delivery device through two layers of sling material near the length indicating feature. In another embodiment, the removing step includes actuating a pusher assembly to slide the sling assembly off of the distal end of the delivery device.

According to another aspect, the invention provides a sling delivery assembly including a delivery device, a guide element and a dilator tube. In one embodiment, the delivery device includes a hollow shaft, and the guide element slidably interfits within the hollow shaft. According to one feature, the dilator tube is sized and shaped to expand a tunnel through patient tissue to ease passage of a sling assembly through the tunnel. According to one feature, the dilator tube has a tapered portion near a distal end for inhibiting a sling assembly from sliding proximally along a substantial portion of the length of the dilator tube. According to another feature, the dilator tube includes an axially extending through lumen for slidably interfitting over the guide element to deliver the sling assembly to an anatomical location in the patient.

In one configuration, the guide element is flexible and deformable, and is formed, for example, as a guide wire. In other configurations the guide element is substantially rigid and nondeformable, and is formed, for example, as a guide rod. The guide element may be substantially straight, or may included one or more curved portions. The length of the guide element may vary as desired, e.g., according to a patient's anatomy or size. A second guide element may be included in the system.

The dilator tube may be flexible and deformable or substantially rigid and nondeformable. The dilator tube may be substantially straight or include one or more curved portions. The various portions may lie substantially in one plane or more than one plane. According to one configuration, the dilator tube is sized and shaped so that the tapered portion can interfit with an opening or a through aperture in a mesh of a sling included in the sling assembly, or with an otherwise suitably configured end of the sling assembly. In another configuration, the dilator tube is sized and shaped so that the tapered portion can interfit with a preformed, structurally reinforced opening or through aperture in an end of a sling included in the sling assembly. The dilator tube may have a constant outside diameter along its entire length, exclusive of the tapered distal portion, or may be tapered along part or all of its length, preferably having a decreasing diameter from a proximal end toward the distal end. The system or delivery assembly may be include a second dilator tube.

According to further aspect, the invention provides a method for delivering a sling assembly to an anatomical location in a patient. In one embodiment, the method includes the steps of inserting a delivery device into the body of the patient, slidably interfitting a guide element into an axially extending through lumen in the delivery device, removing the delivery device from the body of the patient, slidably interfitting over the guide element a dilator tube having a tapered distal portion associated with a first end of the sling assembly to deliver a sling included in the sling assembly to the anatomical location. According to one approach, the same or a second delivery device, guide element, and/or dilator tube may be used to introduce a second end of the sling assembly into the body of the patient on the contralateral side.

In another aspect, the invention is directed to a sling delivery assembly, including a trocar, for delivering a sling assembly to an anatomical location in a patient. In one configuration, the trocar includes a distal tip sufficiently sharp to pierce tissue during sling assembly delivery. According to a further configuration, the trocar has an outer portion extending proximally from the distal tip and including a tapered distal end. In a similar fashion to the above described dilator tube, the tapered distal end of the trocar is sized and shaped to interfit with an opening or a through aperture in an end of a sling and/or sling assembly, and to inhibit the sling and/or sling assembly from sliding proximally along a substantial portion of the length of the trocar.

The trocar may be substantially straight or include one or more curved portions. The various portions may lie substantially in one plane. Alternatively, the various portions may lie in more than one plane. The trocar may have a constant outside diameter along its entire length, exclusive of the tapered distal end. Alternatively, the trocar may be tapered along part or all of its length, preferably having a decreasing diameter from a proximal end toward the distal end. A second trocar may be included in the system.

According to a further aspect, the invention is directed to a method for delivering a sling assembly to an anatomical location in a patient using a trocar. In one embodiment, the method includes the step of interfitting a first end of the sling assembly over a tapered distal end of the trocar, the tapered distal end of the trocar being sharp enough to pierce tissue during sling assembly delivery and being sized and shaped to inhibit the sling assembly from sliding proximally along a substantial portion of the length of the trocar. According to one process, the method includes the step of inserting the distal tip of the trocar, with the first end of the sling assembly interfitted, into the body of the patient to deliver a sling included in the sling assembly to the anatomical location. According to one methodology, the same or a second trocar may be used to introduce a second end of the sling assembly into the body of the patient on the contralateral side.

According to another aspect, the invention provides a sling assembly including an implantable sling, an association loop, and a dilator tube. The association loop is formed from a mono- or multi-stranded filament having first and second ends. The dilator tube includes through lumen extending between proximal and distal ends. The dilator tube also includes an aperture in a side wall located intermediate to the proximal and distal ends. The first end of a loop filament passes though an end of the sling. The first and second ends of the loop filament then pass into the proximal end of the dilator tube. The first end of the loop filament extends through and passes out the distal end of the dilator tube. The second end of the loop filament exits the dilator tube via the aperture in the sidewall. The first and second ends of the loop filament are affixed together at the proximal end of the dilator tube. The sling assembly may include another association loop and dilator tube, similarly associated with the other end of the sling. In some embodiments, the distal ends of the dilator tube are open to enable them to slidably interfit onto the shaft of a delivery device. However, in alternative embodiments, the proximal ends of the dilator tubes include substantially closed tapered ends and do not require any additional delivery device for sling delivery. However, they may also be employed with a delivery device.

In another aspect, the invention provides a method for delivering a sling to an anatomical location in a patient including the steps of inserting a dilator tube associated with an end of a sling assembly via an association loop into the body of a patient to deliver the sling to the anatomical location, making a single cut in the association loop at a proximal end of the dilator tube, pulling on a cut end of the association loop at the proximal end of the dilator tube to remove the association loop from the body of the patient and to disassociate the dilator tube from the sling assembly, and removing the dilator tube from the body of the patient.

According to a feature of the invention, the sling delivery systems and devices of the invention may be sized and shaped for abdominal, transvaginal, or transobtural procedures. Additionally, the methods of the invention may include positioning at least one of first and second ends of a sling and/or sling assembly in front of the pubic bone, behind the pubic bone, near the pubic bone, and/or near or through an obturator foramen.

Other aspects and advantages are described below.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIGS. 2A and 2B depict an implantable sling according to an illustrative embodiment of the invention.

FIGS. 3A-3C depict various configurations of a sling delivery system according to an illustrative embodiment of the invention.

ILLUSTRATIVE DESCRIPTION

Figures 1A, 1B:
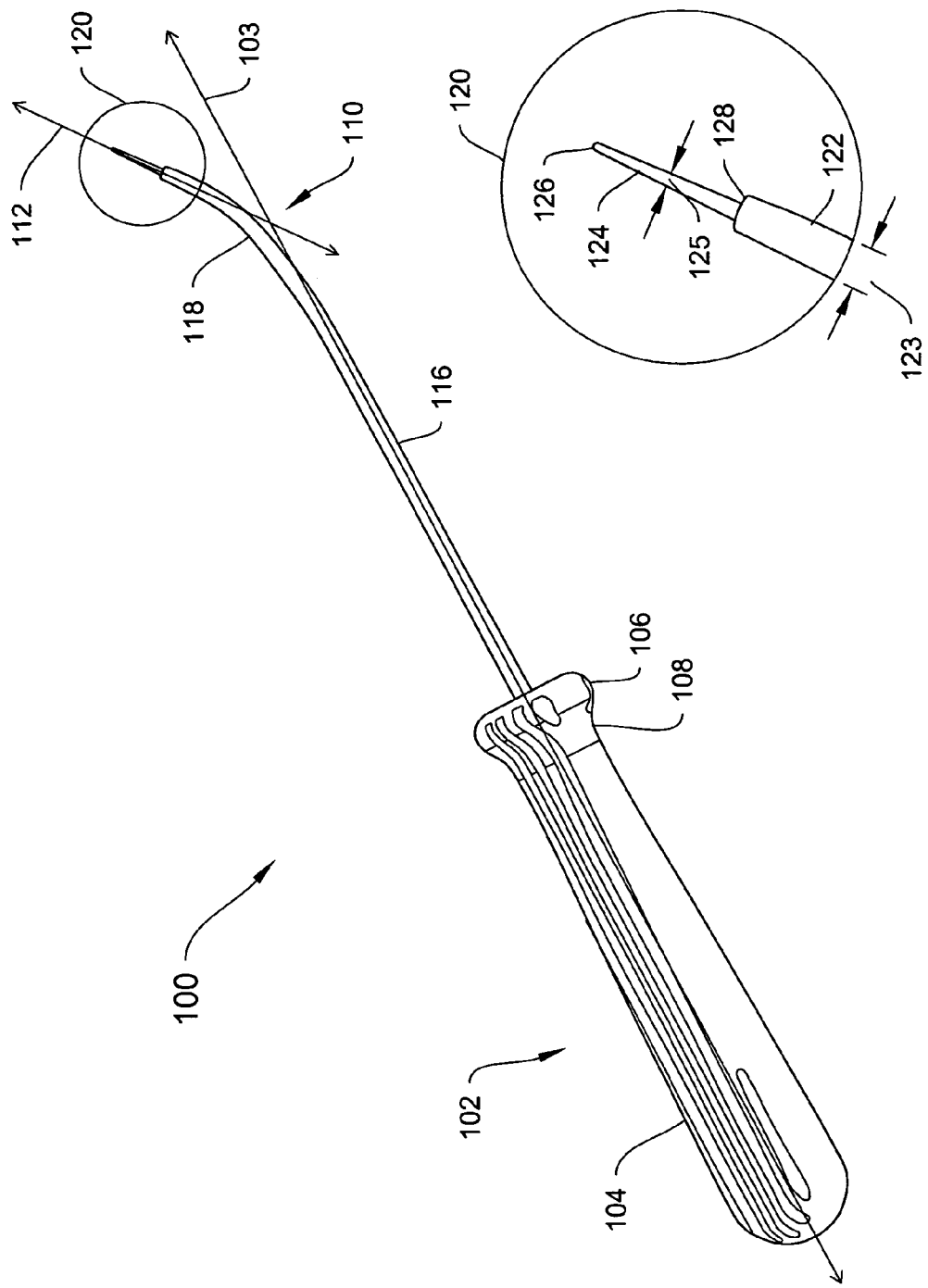
FIGS. 1A and 1B depict a device for delivering a sling to an anatomical site in a patient according to an illustrative embodiment of the invention.

In general, the invention is directed to systems and methods for the treatment of urinary incontinence. In one illustrative embodiment, the invention provides improved systems and methods for delivering a medical implant to an anatomical site of a patient. In a preferred embodiment, the medical implant is a sling for treating urinary incontinence and it is delivered to the periurethral tissues of either a female or male patient. As described below in more detail, in various illustrative embodiments, the invention provides systems and methods for delivering a supportive sling to the periurethral tissue of a patient, without the need for abdominal or ishiopubic incisions. According to other illustrative embodiments, the invention makes it easier for a medical operator to accurately place the supportive sling at a desired anatomical location. In other illustrative embodiments, the invention makes it easier for a medical operator to disassociate a sling from a delivery device and/or a remaining portion of a sling assembly.

Without limitation, examples of slings, sling assemblies, delivery devices and implantation approaches with features that may be employed in illustrative embodiments of the invention are disclosed in U.S. Pat. No. 6,666,817, entitled "Expandable surgical implants and methods of using them," U.S. Pat. No. 6,669,706, entitled "Thin soft tissue surgical support mesh," U.S. Pat. No. 6,375,662, entitled "Thin soft tissue surgical support mesh," U.S. Pat. No. 6,042,592, entitled "Thin soft tissue surgical support mesh," U.S. patent application Ser. No. 10/015,114, entitled "Devices for minimally invasive pelvic surgery," U.S. patent application Ser. No. 10/774,826, entitled "Devices for minimally invasive pelvic surgery," U.S. patent application Ser. No. 10/093,398, entitled "System for implanting an implant and method thereof," U.S. patent application Ser. No. 10/093,498, entitled "System for implanting an implant and method thereof," U.S. patent application Ser. No. 10/093,371, entitled "System for implanting an implant and method thereof," U.S. patent application Ser. No. 10/093,424, entitled "System for implanting an implant and method thereof," U.S. patent application Ser. No. 10/093,450, entitled "System for implanting an implant and method thereof," U.S. patent application Ser. No. 10/094,352, entitled "System for implanting an implant and method thereof," U.S. patent application Ser. No. 10/631,364, entitled "Bioabsorbable casing for surgical sling assembly," U.S. patent application Ser. No. 10/641,376, entitled "Spacer for sling delivery system," U.S. patent application Ser. No. 10/641,487, entitled "Systems, methods and devices relating to delivery of medical implants," U.S. patent application Ser. No. 10/642,395, entitled "Systems, methods and devices relating to delivery of medical implants," U.S. patent application Ser. No. 10/642,397, entitled "Systems, methods and devices relating to delivery of medical implants," U.S. patent application Ser. No. 10/832,653, entitled "Systems and methods for sling delivery and placement," U.S. patent application Ser. No. 10/939,191, entitled "Devices for minimally invasive pelvic surgery," U.S. Provisional Patent Application Ser. No. 60/508,600, filed on Oct. 3, 2003 and U.S. Provisional Patent Application Ser. No. 60/569,300, filed on May 6, 2004, and U.S. patent application Ser. No. 10/957,926, entitled "Systems and methods for delivering a medical implant to an anatomical location in a patient," filed on Oct. 4, 2004, the entire contents of all of which are incorporated herein by reference.

FIG. 1A depicts a device 100 for delivering a sling to an anatomical site in a patient according to an illustrative embodiment of the invention. The device 100, as depicted, includes a handle 102 and a shaft 110. The handle 102 includes a proximal end 104 and a distal portion 106 and extends substantially along an axis 103. The handle 102, as depicted, is substantially straight and tapers inward from the proximal end 104 to a distal location 108. The distal portion 106 of the handle 102 tapers outward from the distal location 108 to help prevent a medical operator's hand from slipping distally while using the device by grasping the handle 102. The shaft 110, as depicted, includes a first substantially straight proximal portion 116 attached to and extending distally from the distal end 106 of the handle 102, substantially along the axis 103. The illustrated shaft 110 also includes a curved portion 118 that extends distally from and curves away from the substantially straight proximal portion 116, and a second substantially straight portion 120 extending distally from the curved portion 118 and substantially along an axis 112. In illustrative embodiments, the axes 103 and 112 form a non-orthogonal angle relative to each other and lie substantially in a single plane. However, this need not be the case, and any suitable delivery device may be employed with the invention.

In certain embodiments, the shaft 110 may be, for example, substantially straight or may include one or more curved sections. Additionally, the shaft 110 may lie substantially in one plane or may be shaped to lie in multiple planes. The shaft 110 may be of substantially constant outside diameter or may include portions of differing outside diameters. In various embodiments, the shaft may include hooked and/or helical portions. The shaft may also be configured in various ways and/or include various features as described in the above-referenced patents and patent applications. Similarly, the handle 102 may also be configured in various ways and/or include various features as described in, e.g., U.S. Provisional Patent Application Ser. Nos. 60/508,600 and 60/569,300, the disclosures of which are herein incorporated by reference.

FIG. 1B shows a magnified view of the distal portion 120 of the device 100 depicted in FIG. 1A. The distal portion 120 includes a substantially straight proximal section 122 having an outside diameter 123, and a substantially straight distal section 124 extending distally from the proximal section 122 and having an outside diameter 125. The distal section 124 terminates in a distal tip 126. In illustrative embodiments, the diameter 125 is substantially smaller than the diameter 122, forming a radially extending shoulder 128 between the proximal section 122 and the distal section 124. According to one feature, the shoulder 128 inhibits or impedes an end of a sling assembly slidably engaged or associated with the distal section 124 from sliding proximally along the curved section 118 and first straight section 116 of the shaft 110 during implantation of the sling assembly. The distal tip 126 may be sharp enough to pierce tissue, or alternatively, relatively blunt. Additionally, the distal tip 126 may have a conical or any other suitable shape.

In one configuration, the shoulder 128 extends around the entire circumference of the shaft 110. In other configurations, the shoulder 128 extends around only a portion of the circumference. In both cases, the shoulder 128 extends far enough to provide a protuberance of sufficient size to impede the sling assembly end from sliding proximally along a substantial portion of the length of the shaft 110.

In alternative embodiments, the distal portion 120 may taper towards the distal end 126. The tapered distal portion 120 may have an outside diameter that gradually decreases distally, instead of an abrupt decrease in outside diameters, such as the diameters 123 and 125 depicted in FIG. 1B. The tapered distal portion 120 may also prevent an end of a sling assembly from sliding proximally during implantation of the sling assembly after the end of the sling assembly is hooked onto the distal portion 120. The distal portion 120 may, for example, include a slotted distal tip, such as an L-groove of the type disclosed in the above incorporated patents and patent application, or a fork-like feature, such as depicted in FIG. 12B, for associating a sling assembly end with the distal end 120 of the shaft 110.

FIG. 2A depicts an implantable sling 200 according to an illustrative embodiment of the invention. As depicted, the sling 200 has two ends 202 and 204. The sling 200 also, optionally, has a backbone structure including an anti-deformation filament 206, which threads axially through the sling 200. The filament 206, alternatively, may be threaded along a portion of the length of the sling 200. The filament 206 may be formed, for example, from a suture or any other biocompatible materials. As depicted, the illustrative filament 206 is knotted at and extends past each of the ends 202 and 204 of the sling 200. In this embodiment, the filament 206 may provide a tensioning mechanism for maintaining or adjusting tensioning of the sling 200 during and/or after implantation. As also depicted, the filament 206 is woven into the mesh of the sling 200 in a zig-zag or ragged pattern, providing a certain amount of available slack in the filament 206. In this configuration, the filament 206 enables the sling 200 to stretch to some extent (e.g., until all of the slack in the filament 206 is used), but also reduces the likelihood of the sling 200 distorting due to over stretching during implantation. The filament 206 may be left in the body of a patient, along with the sling 200 after implantation. Alternatively, in some configurations (e.g., those where the filament is not knotted to the sling ends 202 and 204), the filament 206 may be removed from the body of the patient after sling implanting.

The sling 200, optionally, includes a center-indicating feature 208 and other length- and/or position-indicating features 210 along its length. According to a preferred embodiment, the center-indicating feature 208 is distinguishable from the length-indicating features 210, for example, being differently sized and/or colored. Additionally, the length-indicating features 210 are preferably easily distinguishable from each other, for example, also being differently sized and/or colored. According to one configuration, the length-indicating features 210 are spaced at regular, known intervals. The features 208 and 210 may indicate to a medical operator the position of the sling 200 during implantation and/or enable the medical operator to adjust the length of the sling 200 prior to or during implantation. The features 210 may also be employed to indicate the effective length of the sling 200 subsequent to implantation.

FIG. 2B shows a magnified view of the sling end 202. As shown, the sling end 202 included a preformed, structurally reinforced through aperture 212 for slidably interfitting with a distal end of a delivery device, such as the delivery device 100. The aperture 212 also provides a convenient location for attaching, for example, tying to the filament 206.

In certain embodiments, an implantable sling 140 does not include any openings/apertures other than those created by the mesh structure itself. One or more of such mesh openings may be used instead of a preformed through aperture, for slidably associating the sling 200 with a delivery device, such as the delivery device 100 depicted in FIG. 1A or any other suitable delivery device, such as those depicted throughout this disclosure.

With continued reference to FIG. 2A, in some illustrative embodiments, the sling 200 has a length of about 10 to about 15 cm (about 4-6 inches) and a width of about 1 to about 3 cm, though the length and width of the sling 200 can be adapted to the body part of the patient that requires support. By way of example, in some embodiments, the sling 200 is about 45 cm in length. The sling 200 may be substantially rectangular, as illustrated in FIG. 2A, or have another suitable shape. The sling 200 may have a uniform thickness over the entire length and/or width of sling 200. Alternatively, the thickness can be suitably varied at one or more locations. The thickness of the sling material may range, for example, from about 0.02 to about 0.10 cm. In one illustrative embodiment, the sling 200 is formed from a strip of mesh with any of a plurality of configurations of knits, weaves, or braids.

The sling 200 may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials can include polyglycolic acid, polylactic acid, and other suitable absorbable synthetic materials. Alternatively, the material for the sling 200 may be derived from mammalian tissue(s) or a combination of mammalian tissue(s) and synthetic material(s). The sling material may be fabricated from one or more yarns, which yarns may be made from one or more materials. The sling 200 may incorporate or be coated with one or more agents to provide a therapeutic effect, for example, to reduce discomfort, to reduce the chance of infection and/or to promote tissue growth.

Referring back to FIG. 2A, in one embodiment, the edge regions of the sling 200 may be configured differently depending on their intended placement in the body of the patient. For example, in one illustrative embodiment a midsection 214 of the sling 200 is located at an anatomical site, such as a midurethral or bladder neck location in the periurethral tissue, that needs to be supported. The midsection 214, in one illustrative embodiment, has smooth or rounded edges, hereinafter also referred to as "non-tanged." According to a further illustrative embodiment, other sections of the sling 200 may include tangs (e.g., sharp projections or frayed edges) 216. The tangs 216 are generally useful for anchoring the sling 200 and encouraging tissue growth into the sling 200. Anchoring the sling 200 in this manner generally obviates the need for additional sutures to hold the sling 200 in place.

The tanged and non-tanged edges of sling 200 may be formed in a plurality of ways. For example, the sling 200 may be cut from a woven sheet, in which case the edges are initially tanged along the entire length of the sling 200. One or more non-tanged sections may be formed by any process that smoothes, rounds or removes the sharp edges of the tangs 216. For example, the tangs 216 may be heat-smoothed by burning or melting. In one embodiment, the non-tanged section 214 has a length of about 1 to about 5 cm, preferably about 2 to about 2.5 cm, on either or both sides of the center line as marked by the center feature 208. Providing one or more non-tanged sections, which may be in close proximity to a sensitive anatomical site in the patient, can enhance the comfort level of the patient and reduce the potential for the edges of the tangs to erode or irritate, for example, the urethra.

Alternatively, the sling 200 may be formed from a woven tape having the approximate finished width of the sling 200. The smooth sides of the tape can then be trimmed off to produce and tanged sections, such as the tanged section 216.

In certain embodiments, the sling 200 terminates at free ends 202 and 204. In certain embodiments, the sling 200 is part of a sling assembly, which optionally includes a sleeve enclosing at least partially the sling 200. In a preferred embodiment, the free ends 202 and 204 do not attach to the sleeve or anything else, thus enabling a medical operator to pull on the ends of the sleeve enclosing at least partially the sling 200 during placement of the sling 200, without risk of stretching, curling or otherwise deforming the sling 200.

The sleeve enclosing at least partially the sling 200 may be made, for example, from one or more absorbent materials, such as a sponge-like material, that can optionally be presoaked in a drug solution, for example, in an antibiotic solution. In preferred embodiments, the sleeve enclosing at least partially the sling 200 may be made from bioabsorbable materials, and the bioabsorbable sleeve does not require removal subsequent to placement or implantation of the sling 200. In another embodiment, the sleeve may be made from a non-wettable material, such as polypropylene, polyethylene, polyester, polytetrafluoroethylene (available from DuPont Corporation, Wilmington, Del., under the trademark TEFLON®), TYVEK V, MYLAR®, or co-polymers thereof. The non-wettable materials can also be pretreated with a therapeutically effective drug coating. The sleeve can be transparent so that an operator will be able to see the implantable sling 200 inside the sleeve. In alternate embodiments, the sleeve may include a break or rupture location, such as a perforation near the center of the sleeve, allowing the sleeve to be separated after placement of the sling 200.

A medical operator needs to exercise care that the sling 200 has the appropriate tension to serve its remedial purpose, for example, providing needed suspension to the urethra or bladder neck, or applying tension to the periurethral tissues, e.g., the urethral sphincter. For example, if there is excessive friction between the sling 200 and the interior wall of a sleeve enclosing at least partially the sling 200, then the sling 200 may be over tensioned and may stretch, causing the sling 200 to wrap too tightly around the target periurethral tissues or causing distortion in the sling 200, for example, curling of sides of the sling 200 along its length. As discussed above, the filament 206 aids in avoiding such sling distortion issues.

Figure 3A:
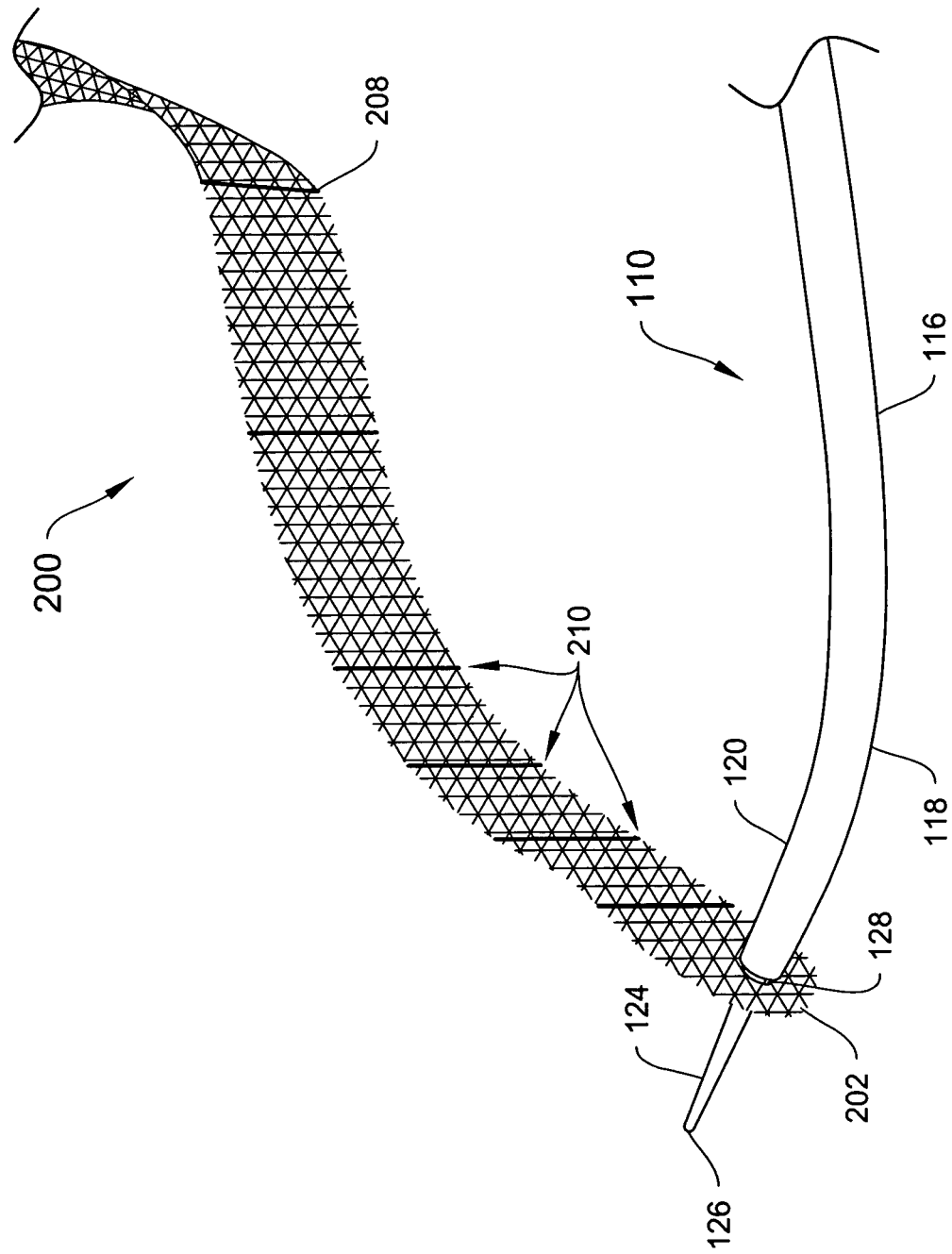
Figure 3C:
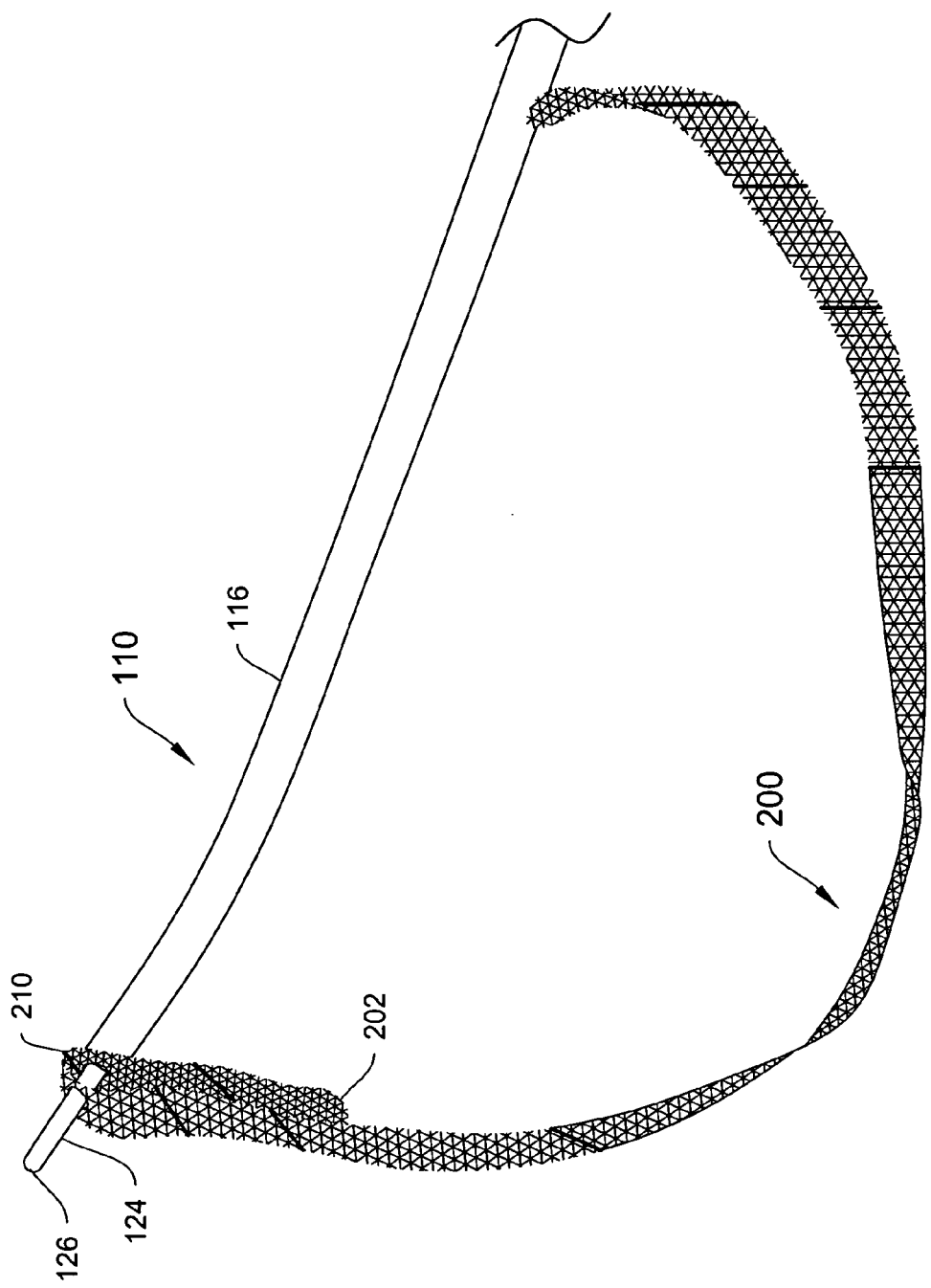

FIGS. 3A-3C depict the sling 200 associated with the distal end 120 of the shaft 110 according to various illustrative embodiments of the invention. More particularly, FIG. 3A depicts the sling 200 having the end 202 associated with the distal portion 120 of the shaft 110 of a delivery device of the invention 100 of FIG. 1. In this particular embodiment, the distal tip 126 of the shaft 110 slidably interfits through the preformed aperture 212 in the sling end 202. As previously described, the shoulder 128 in the distal portion 120 of the shaft 212 impedes the sling end 202 from sliding proximally along the shaft 110.

In the alternative embodiment of FIG. 3B, the distal tip 126 interfits through an opening created by the natural structure of the mesh material at one of the length-indicating features 210. In this way, a medical operator can effectively change the length of the sling 200 based, for example, on the particular anatomy of the patient and/or the particular application. According to one feature of this embodiment, the end portion of the sling 218 may be trimmed off prior to implantation.

FIG. 3C shows another alternative embodiment where the sling end 202 is folded back along the length toward the center of the sling 200 at a particular length-indicating feature 210 to adjust the length of the sling 200 prior to implantation. According to a feature of this embodiment, the distal tip 126 of the shaft 110 slidably interfits through two layers of mesh near the feature 210. This configuration both effectively shortens the length of the sling 200 and provides a reinforced double layered sling section for slidable association with the distal tip 126 of the shaft 110.

Figure 4:
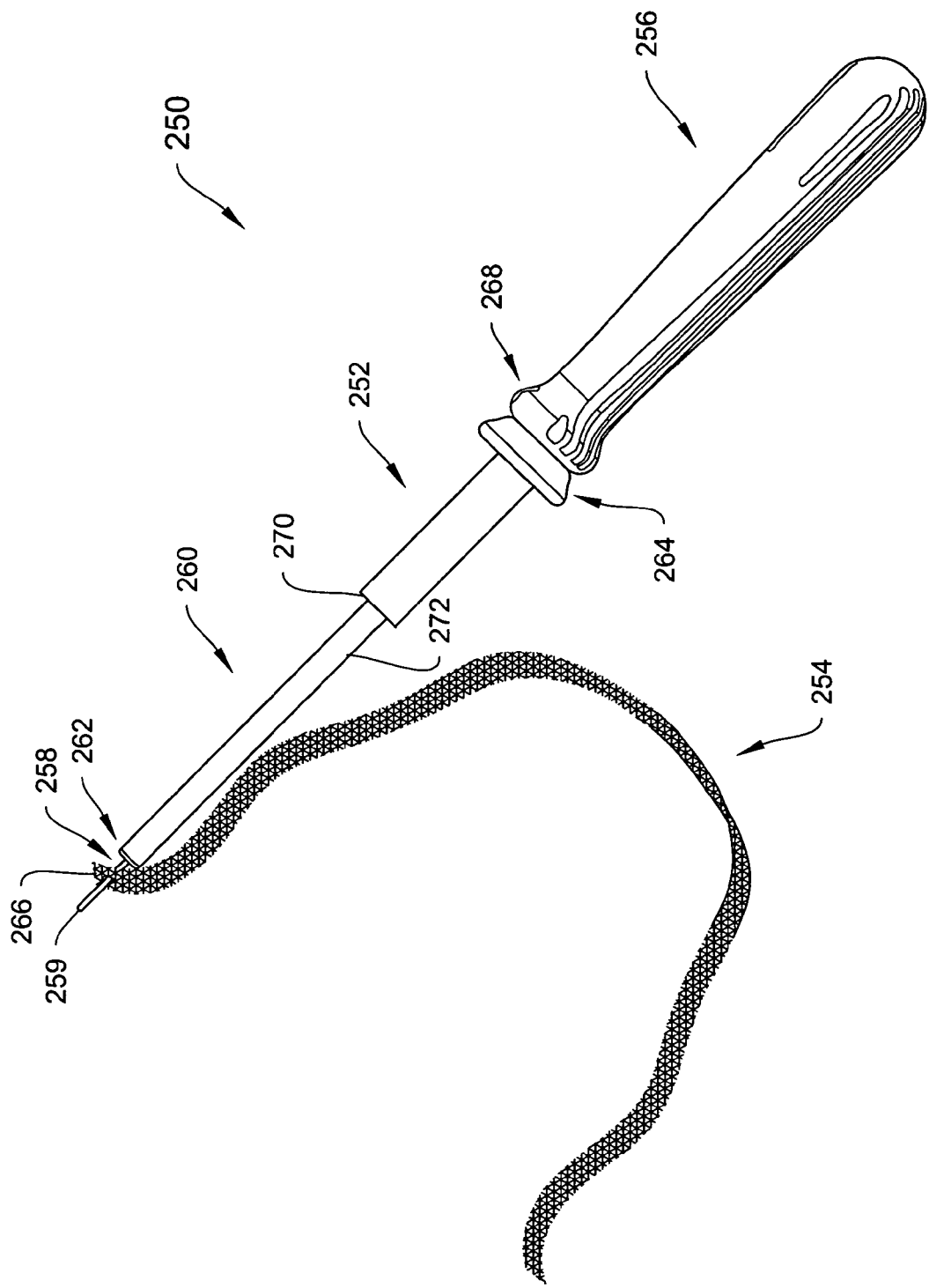
FIG. 4 depicts an illustrative sling delivery system employing a pusher assembly and a sling of the type depicted in FIGS. 2A and 2B.

FIG. 4 depicts another illustrative sling delivery system 250 including a sling delivery device 252 and a sling 254. The sling 254 is, for example, of the type 200 depicted in FIGS. 2A and 2B. As such, it may slidably interfit with the delivery device 252 in the same fashion as depicted in FIGS. 3A-3C with respect to the delivery device 100. The sling delivery device 252 may be shaped and sized in any of the ways previously described with respect to the delivery device 100 of FIGS. 1A and 1B. As in the case of the delivery device 100, the delivery device 252 includes a handle 256 and a shaft 258 extending distally from the handle 256. The shaft 258 includes a distal tip 259 for slidably interfitting with the sling end 266. The shaft 258, including distal tip 259, may be sized and shaped in any of the ways previously described with respect to FIGS. 1A and 1B.

An additional feature of the embodiment of FIG. 4 is that the delivery device 252 includes a pusher assembly 260. The pusher assembly 260 slidably interfits over the shaft 258 and abuts the distal end 268 of the handle 256. A distal end of the pusher assembly 260 forms a radially outwardly extending shoulder 262 around the circumference of the shaft 258 and functions in a similar fashion to the proturberence 128 of FIG. 1B to impede the sling end 266 from sliding proximally along a substantial portion of the length of the shaft 258. The pusher assembly 260 also includes a stop surface 270 which extends around the circumference of the pusher assembly 260. The stop surface 270 has an increased diameter relative to a distal portion 272 of the pusher assembly 260 and causes increased resistance with body tissue of the patient when being inserted into such tissue. This feature enables the medical operator to determine the length of the shaft 258 that has penetrated the body tissue of the patient and/or prevent the shaft 266 from penetrating to a deeper extend than desired. When the sling end 266 is placed at a desired anatomical location, the medical operator pushes the actuator 264 of the pusher assembly 260 in a distal direction, causing the shoulder 262 to push against the sling end 266 to slide the sling end 266 distally off the distal tip 259 of the shaft 258. In one configuration, the actuator 264 may be held while the handle 256 is withdrawn to deposit a sling or sling assembly without further tension.

According to another illustrative embodiment, the invention provides a method for delivering a sling or a sling assembly to an anatomical location in a patient. The method may employ a delivery device and sling or a sling assembly, such as the delivery devices 100 and 250 and the slings 200 and 254 described above. In one illustrative embodiment, the method includes the steps of sliding a distal end of a delivery device into a sling assembly end, impeding the sling assembly end from sliding proximally along a substantial length of the delivery device, introducing the distal end of the delivery device and the sling assembly end into the body of the patient, and removing the distal end of the delivery device from the sling assembly to deliver the sling to the anatomical location in the patient. According to a further illustrative embodiment, the step of inserting includes inserting the distal end of the delivery device into the sling assembly at a length indicating feature. According to another illustrative embodiment, the method includes the step of folding an end of a sling included in the sling assembly lengthwise at a length indicating feature toward the center of the sling to adjust the length of the sling, and the step of sliding includes sliding the distal end of the delivery device through two layers of sling material near the length indicating feature. According to the illustrative embodiment, the removing step may include actuating a pusher assembly to slide the sling assembly end off of the distal end of the delivery device. According to other illustrative features, the above described methodology may be employed via an initial abdominal incision, ishiopubic incision or transvaginal incision.

In one embodiment, the method includes positioning at least one of first and second ends of a sling included in the sling assembly in front of the pubic bone (i.e., pre-pubicly). In an alternative embodiment, the method includes positioning at least one of the first and second ends of the sling behind the pubic bone (i.e. supra-pubicly). In another embodiment, the method includes positioning at least one of the first and second ends of the sling near the pubic bone. In other embodiments, the method includes positioning at least one of the first and second ends of the sling near or through an obturator foramen (i.e., transobturally).

Figure 5:
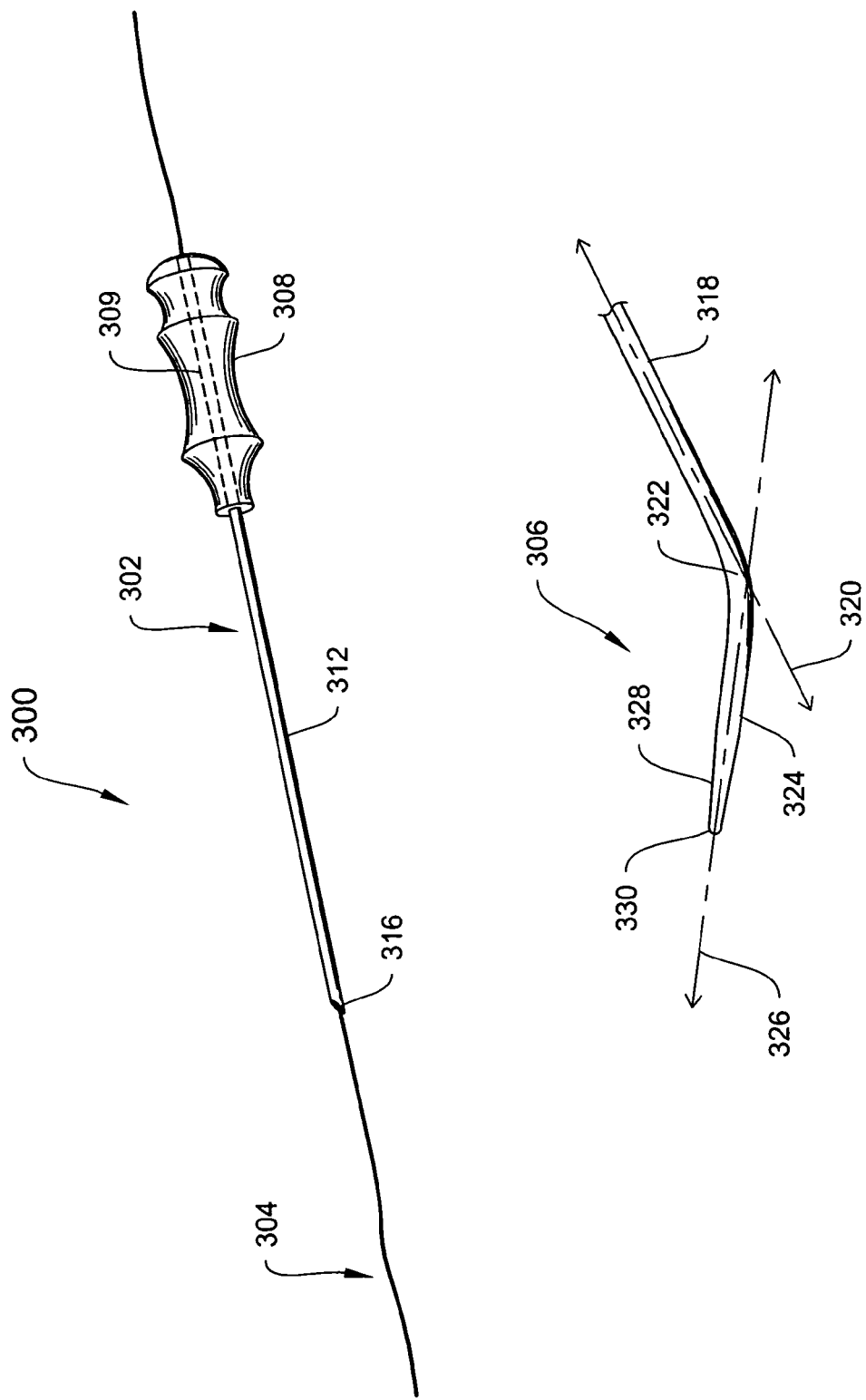
FIG. 5 depicts a sling delivery assembly employing a delivery device, a guide element, and a dilator tube according to another illustrative embodiment of the invention.

FIG. 5 depicts a sling delivery assembly 300 employing a delivery device 302, a guide element 304, and a dilator tube 306 according to another illustrative embodiment of the invention. The delivery device 302, as depicted, also includes a handle 308 located near the proximal end of the device 302. In one configuration, the handle 308 includes a Luer-Lok-like feature. In other configurations, the handle 308 may attach, at or near the proximal end, to another handle element to provide a medical operator with ease in grasping the delivery device 302. According to the illustrative embodiment, the handle 308 includes an axial extending through lumen 309 sized for slidably interfitting over the guide element 304.

The illustrative delivery device 302 also includes a hollow shaft 312 extending distally from the handle 308, in fluid communication with the through lumen 309, and having an inside diameter sized to allow for slidably interfitting the shaft 312 over the guide element 304. The inside diameter of the shaft 312 may be constant or varying along its length. The hollow shaft 312 may be substantially straight along its entire length. Alternatively, the hollow shaft 312 may include one or more curved sections. In certain configurations, the distal end 316 of the hollow shaft 312 is pointed and/or sharp enough to pierce tissue and create a passage within the body of a patient.

According to one illustrative embodiment, the guide element 304 is flexible and deformable, and is formed, for example, as a guide wire. In other configurations, the guide element 304 is substantially rigid and nondeformable, and is formed, for example, as a guide rod. The guide element 304 may be substantially straight, or may included one or more curved portions. The length of the guide element 304 may vary as desired, e.g., according to a patient's anatomy or size. A second guide element 304 may be included in the system.

The dilator tube 306, as depicted, includes a substantially straight proximal portion 318 extending along a first axis 320, a curved section 322 extending distally from the proximal portion 318 and away from the first axis 320, and a substantially straight distal portion 324 extending distally from the curved section 322 and along a second axis 326. The first axis 322 and the second axis 326 are at a non-orthogonal angle relative to each other.

According to one feature, the dilator tube 306 also includes a tapered distal portion 328 near the distal end 330. The tapered distal portion 328 is sized and shaped to interfit with an opening or a through aperture in a mesh of a sling included in a sling assembly, or with an otherwise suitably configured end of the sling assembly. In another configuration, the dilator tube 306 is sized and shaped so that the tapered portion can interfit with a preformed, structurally reinforced opening or through aperture in an end of a sling included in a sling assembly. In a similar fashion to the delivery devices of FIGS. 1A-4, the tapered distal portion 328 is sized and shaped also to impede a sling assembly end from sliding proximally along a substantial portion of the length of the dilator tube 306.

According to another feature, the dilator tube 306 includes an axially extending through lumen for slidably interfitting over the guide element 304 for delivering a sling or a sling assembly to an anatomical location in a patient. According to one configuration, the axially extending lumen of the dilator tube 306 has a substantially constant cross-sectional diameter along its entire length. According to another configuration, the cross-sectional diameter of the axially extending lumen of the dilator tube 306 varies along its length.

The dilator tube 306 may be flexible and deformable or substantially rigid and nondeformable. Although depicted as including a curved portion 322, the dilator tube 306 may be substantially straight or include one or more curved portions. The various portions may lie substantially in one plane or in more than one plane. The dilator tube 306 may have a constant outside diameter along its entire length, exclusive of the tapered distal portion 328, or may be tapered along part or all of its length, preferably having a decreasing diameter from a proximal end toward the distal end 330. The delivery assembly 300 may include a second dilator tube 306.

Figure 6:
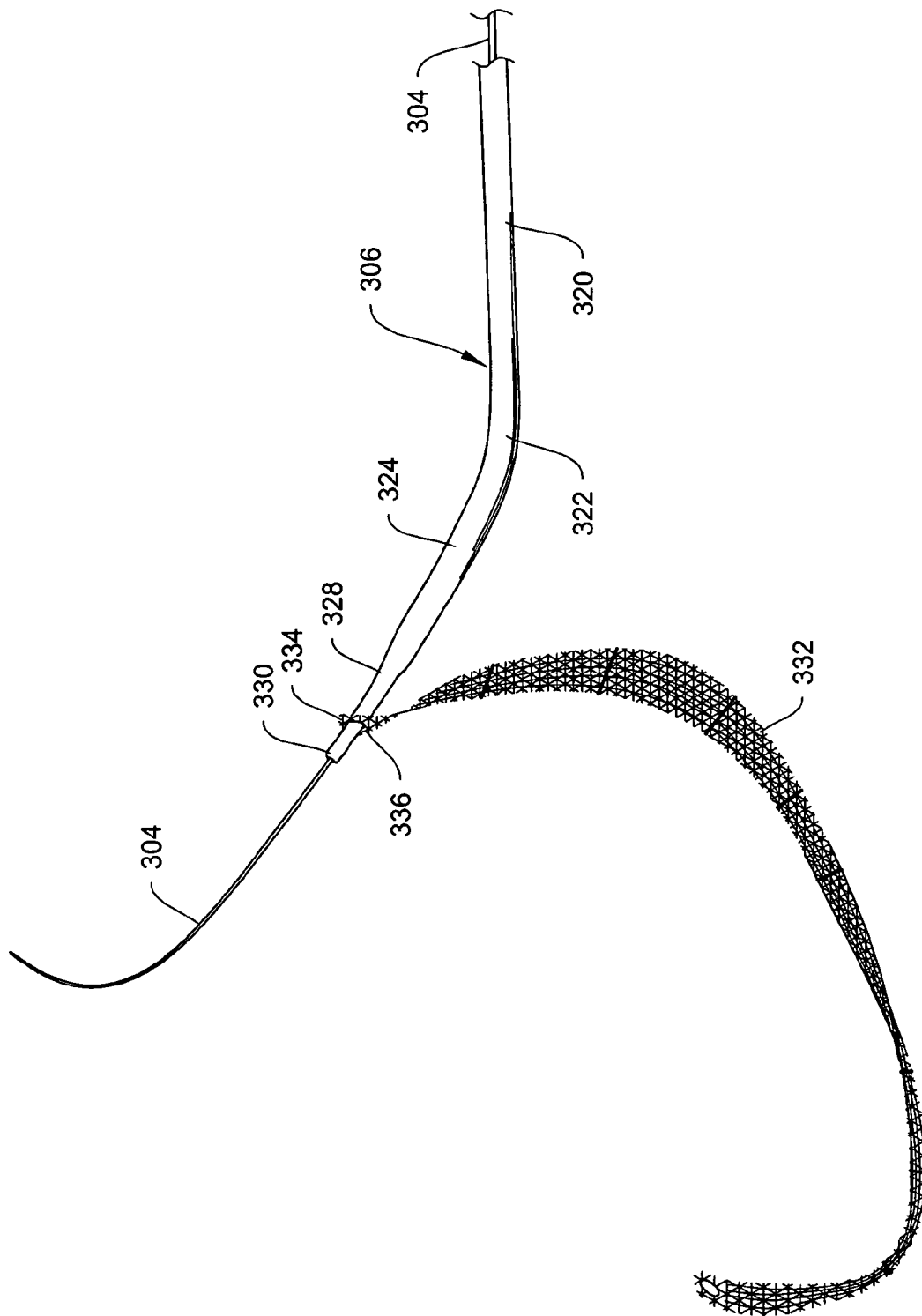
FIG. 6 shows an illustrative sling delivery system employing a delivery assembly of the type depicted in FIG. 5 and an implantable sling of the type depicted in FIGS. 2A and 2B.

FIG. 6 shows the sling delivery assembly 300 of FIG. 5 with the guide element 304 interfitted through the dilator tube 306. FIG. 6 also shows an end 334 of a sling 332 slidably interfitted over the distal tip 330 of the guide tube 306 by way of an opening or the through aperture 336 located at the end 334 of the sling 332. Although not depicted, the sling 332 may have a center feature and various length measurement or position-indicating features along its length, such as depicted in FIG. 2A. The sling 332 may also adopt various other features and configurations as described herein. As depicted, the tapered distal portion 328 of the dilator tube 306 inhibits the end 334 of the sling 332 from sliding proximally along a substantial portion of the length of the dilator tube 306.

According to a further aspect, the invention provides a method for delivering a sling assembly to an anatomical location in a patient by employing a delivery assembly, for example, of the type depicted in FIGS. 5 and 6. In one embodiment, the method includes the steps of inserting a delivery device, for example, the delivery device 302, into the body of the patient, slidably interfitting a guide element, such as the guide element 304, into an axially extending through lumen in the deliver device, removing the delivery device from the body of the patient, slidably interfitting a distal end of a dilator tube, such as the distal end 330 of the dilator tube 306, into an opening in an end of a sling assembly, such as the end 212 of the sling assembly 200, slidably interfitting the distal end of the guide tube over the proximal end of the guide element, and pushing the guide tube proximally along the guide element to deliver a sling included in the sling assembly to the anatomical location. According to one approach, the same or a second delivery device, guide element, and/or dilator tube may be used to introduce a second end of the sling assembly into the body of the patient on the contralateral side. According to other illustrative features, the above described methodology may be employed via an initial abdominal incision, ishiopubic incision or transvaginal incisions.

In one embodiment, the method includes positioning at least one of first and second ends of a sling included in the sling assembly in front of the pubic bone (i.e., pre-pubicly). In an alternative embodiment, the method includes positioning at least one of the first and second ends of the sling behind the pubic bone (i.e. supra-pubicly). In another embodiment, the method includes positioning at least one of the first and second ends of the sling near the pubic bone. In other embodiments, the method includes positioning at least one of the first and second ends of the sling near or through an obturator foramen (i.e., transobturally).

Figure 7:
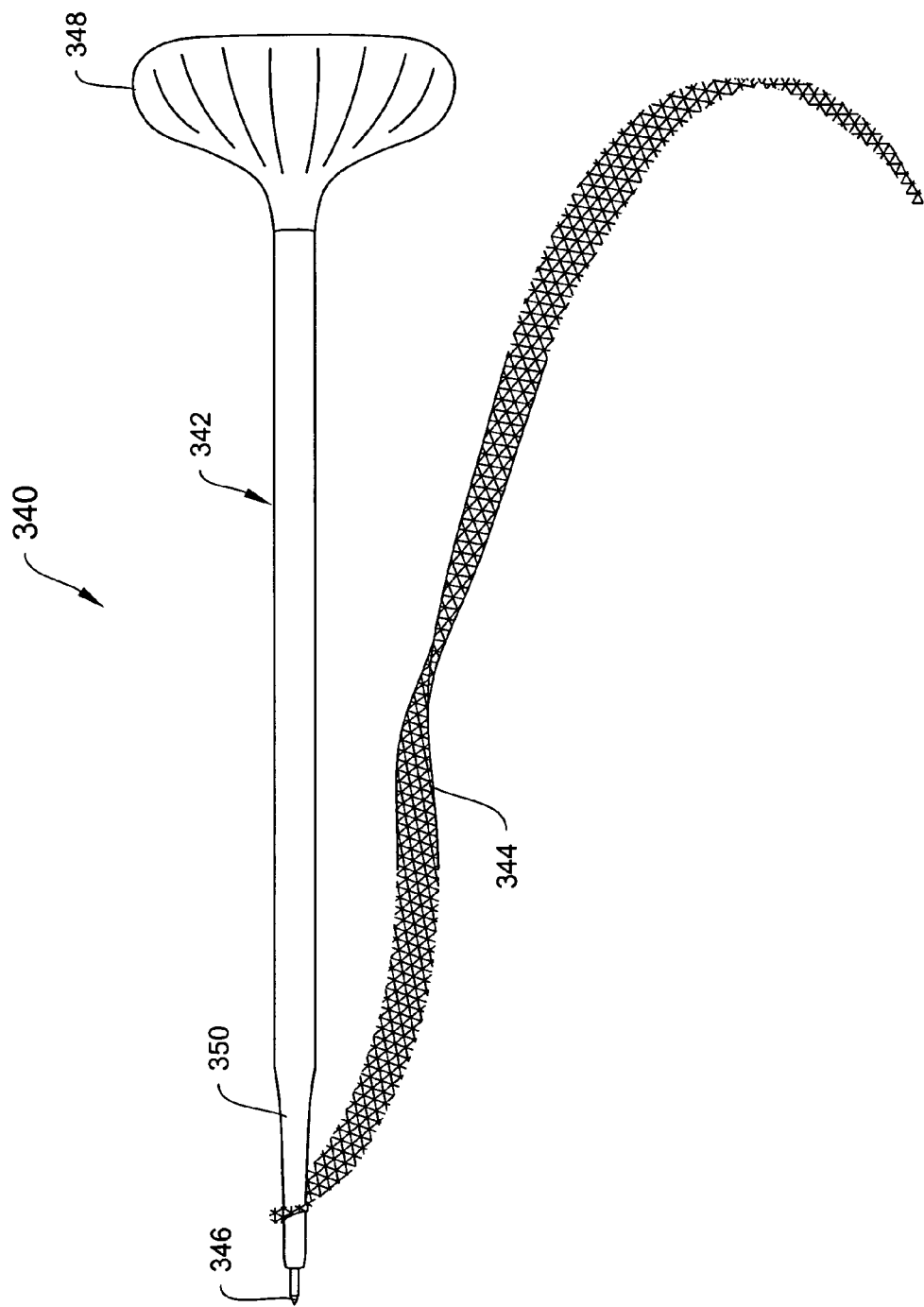
FIG. 7 shows a sling delivery system employing a trocar and an implantable sling of the type depicted in FIGS. 2A and 2B according to another illustrative embodiment of the invention.

FIG. 7 shows a sling delivery system 340 employing a trocar 342 and an implantable sling 344 of the type depicted in FIGS. 2A and 2B according to another illustrative embodiment of the invention. According to the depicted configuration, the trocar 342 includes a distal tip 346 sufficiently sharp to pierce tissue during sling assembly delivery. As shown, the illustrative trocar 342 includes an outer portion extending proximally from the distal tip 346 to a handle 348. The outer portion forms a tapered distal portion 350. In a similar fashion to the above-described tapered distal portion 328 of the dilator tube 306, the tapered distal portion 350 is sized and shaped to interfit with an opening or a through aperture in an end of sling and/or sling assembly, and to inhibit the sling and/or sling assembly from sliding proximally along a substantial portion of the length of the trocar 342.

The trocar 342 may be substantially straight or include one or more curved portions. The various portions may lie substantially in one plane. Alternatively, the various portions may lie in more than one plane. The trocar 342 may have a constant outside diameter along its entire length, exclusive of the tapered distal portion 350 and the tissue piercing distal end 346. Alternatively, the trocar 342 may be tapered along part or all of its length, preferably having a decreasing diameter from a proximal end toward the distal end 346. A second trocar may be included in the system.

According to a further aspect, the invention is directed to a method for delivering a sling assembly to an anatomical location in a patient using a trocar, for example, like the trocar 342 of FIG. 7. In one embodiment, the method includes the step of interfitting a first end of a sling assembly, for example, of the type depicted at 344 in FIG. 7, over a tapered distal end of the trocar, the tapered distal end of the trocar being sharp enough to pierce tissue during sling assembly delivery and being sized and shaped to inhibit the sling assembly from sliding proximally along a substantial portion of the length of the trocar. According to one process, the method includes the step of inserting the distal tip of the trocar, with the first end of the sling assembly so interfitted, into the body of the patient to deliver a sling included in the sling assembly to the anatomical location. According to one methodology, the same or a second trocar may be used to introduce a second end of the sling assembly into the body of the patient on the contralateral side. According to other illustrative features, the above described methodology may be employed via an initial abdominal incision, ishiopubic incision or transvaginal incision.

In one embodiment, the method includes positioning at least one of first and second ends of a sling included in the sling assembly in front of the pubic bone (i.e., pre-pubicly). In an alternative embodiment, the method includes positioning at least one of the first and second ends of the sling behind the pubic bone (i.e. supra-pubicly). In another embodiment, the method includes positioning at least one of the first and second ends of the sling near the pubic bone. In other embodiments, the method includes positioning at least one of the first and second ends of the sling near or through an obturator foramen (i.e., transobturally).

Figure 8:
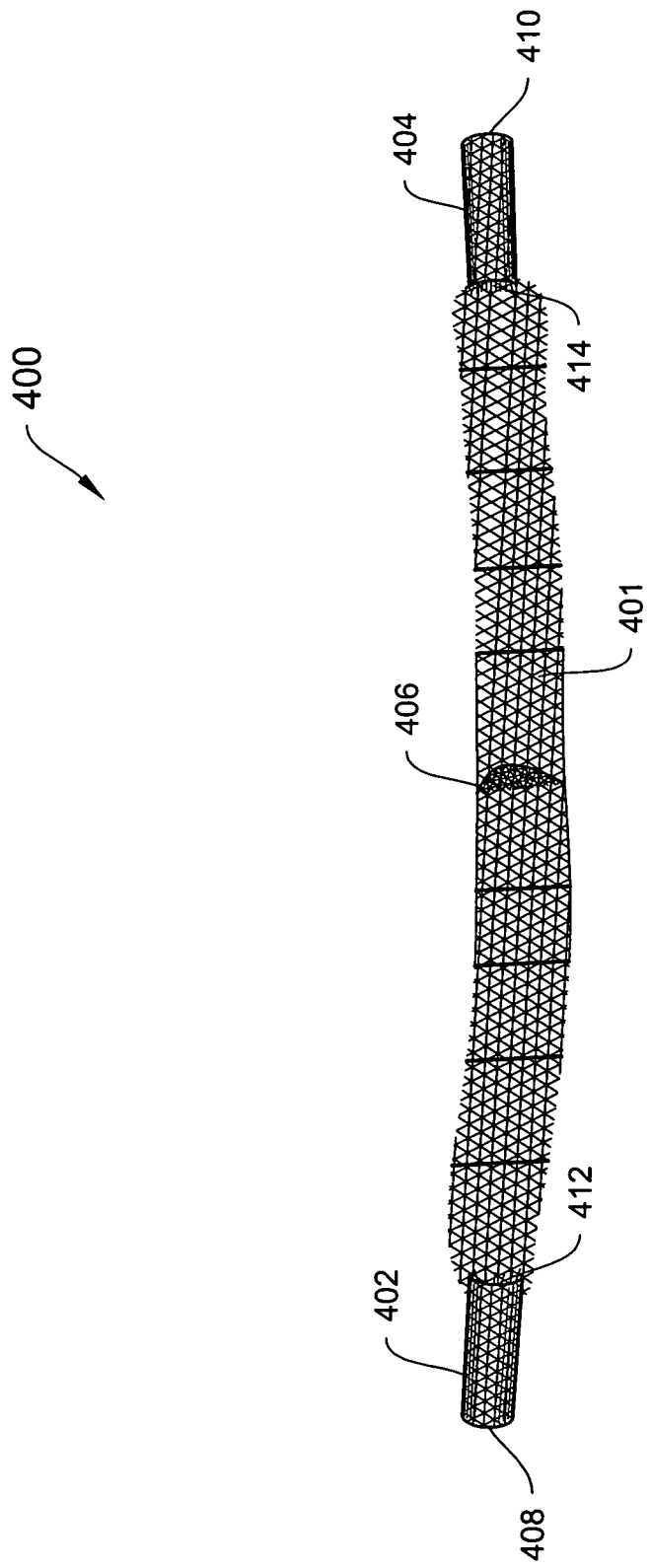
FIG. 8 shows another illustrative sling employing association tubes at its ends for slidably associating the depicted sling with a delivery device.

FIG. 8 shows another illustrative sling assembly 400 employing association tubes 402 and 404 at its ends for slidably associating the depicted sling 400 with a delivery device. The association tubes 402 and/or 404 may taper in a direction toward or away from the midpoint of the sling 400 depending on into which end of the association tube a delivery device shaft is to be inserted. More specifically, an inward taper toward the center location 406 of the sling assembly 400 may be more suitable for a distal end of a delivery device being slidably inserted into the association tubes 402 and 404 via outer most ends 408 and 410, respectively. Whereas, an inward taper away from the center location 406 may be more suitable for a distal end of a delivery device being slidably inserted into the association tubes 402 and 404 via inner most ends 412 and 414. The associate tubes 402 and 404 may be affixed to the ends of the sling assembly 400 by any suitable mechanism, including gluing, heat bonding, shrink tubing or the like. In certain embodiments, the association tubes 402 and 404 are designed to slide onto the shaft of a delivery device of the invention, and preferably the inner diameter of the association tube is larger than the diameter(s) of the shaft or the diameter(s) of at least one section of the shaft, e.g., a distal end of the shaft. It should be noted that, as in the case of the previously discussed sling assemblies, the sling assembly 400 may include a sleeve for enclosing, at least partially, the sling material 401 and the association tubes 402 and 404 may be bonded to any such sleeve rather than the mesh material 401.

Figure 9:
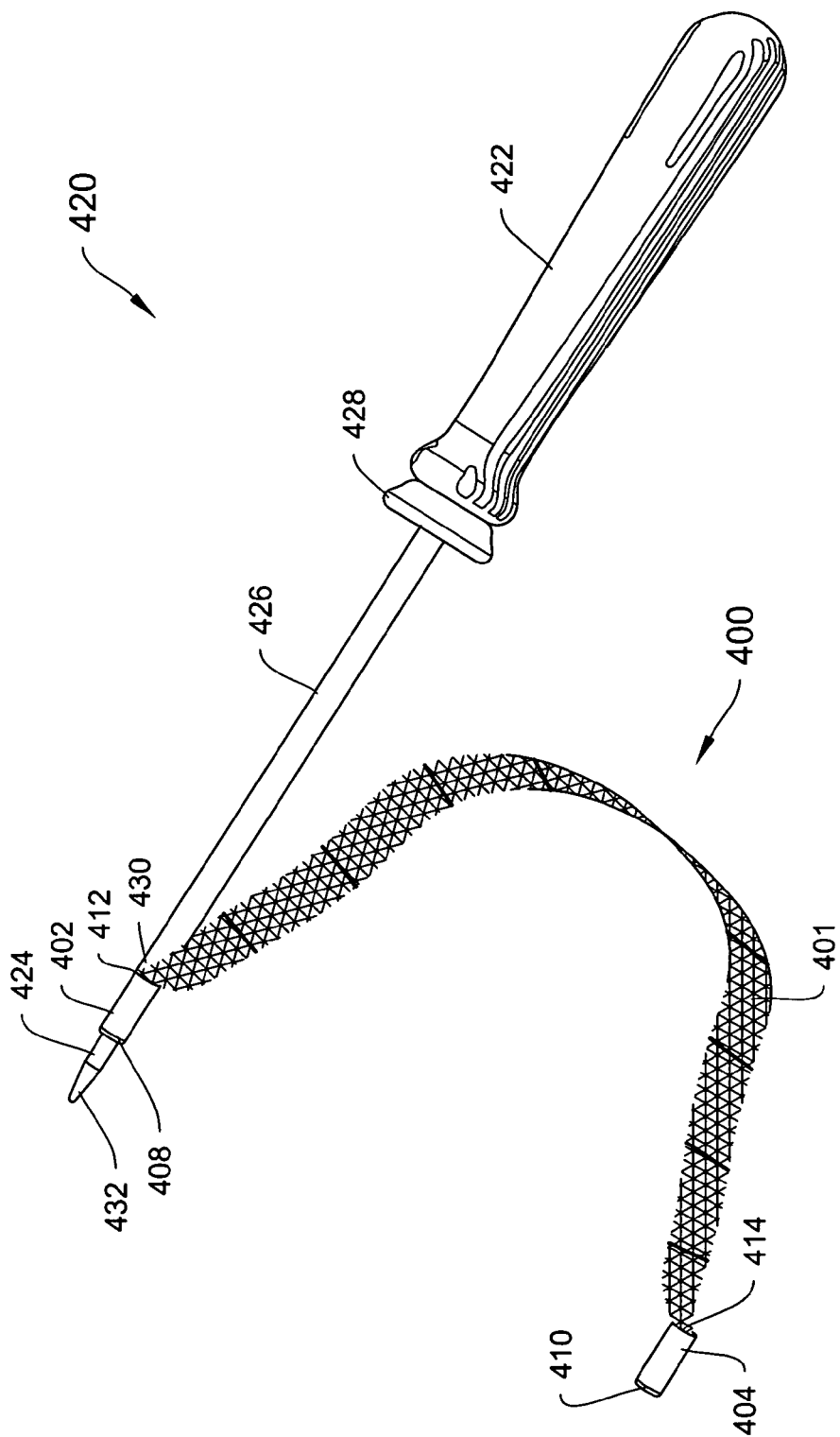
FIG. 9 shows a sling of the type depicted in FIG. 8 slidably interfitted with a delivery device employing a pusher assembly according to an illustrative embodiment of the invention.

FIG. 9 shows the sling assembly 400 of FIG. 8 slidably interfitted with a delivery device 420. The illustrative delivery device 420 includes a handle 422, a shaft 424 extending distally from the handle 422 and a pusher assembly 426 slidably interfitted over the shaft 424. The pusher assembly includes a user actuator 428 at its proximal end, and engages with the inner most end 412 of the association tube 402 at a distal end 430. In this particular illustrative embodiment, the inner most end 412 of the association tube 402 slidably interfits over the distal end 422 of the delivery device 420.

The depicted shaft 402 is substantially straight and terminates at a distal end in a conical tip 432. Alternatively, the shaft 402 may employ a distal tip sufficiently pointed or sharp to pierce through body tissue, or in other alternative embodiments employ a blunt tip. Additionally, the shaft 402 may have one or more curved portions. The shaft 402 is depicted as lying in substantially one plane. Alternatively, the shaft 402 may have various portions that lie in more than one plane.

The pusher assembly 426, as mentioned above, is slidably interfitted over the shaft 424 and slidably actuatable in a distal direction by an operator via the actuator 428 to effectively push the associate tube 402, and thus an end, of the sling 401 off the distal end 432 of the shaft 402. In one configuration of this embodiment, the distal end 430 of the pusher assembly 426 forms a shoulder for impeding the association tube 402 of the sling assembly 400 from sliding proximally along a substantial portion of the length of the shaft 424. In another illustrative configuration, the pusher assembly 426 includes a stop surface, such as the stop surface 270 of FIG. 4, for aiding a medical operator in determining how much of the length of the shaft 424 has penetrated the body tissue of a patient. This feature also aids the medical operator to avoid causing the shaft 424 to penetrate the patient body tissues further than desired.

Figures 10A, 10B:
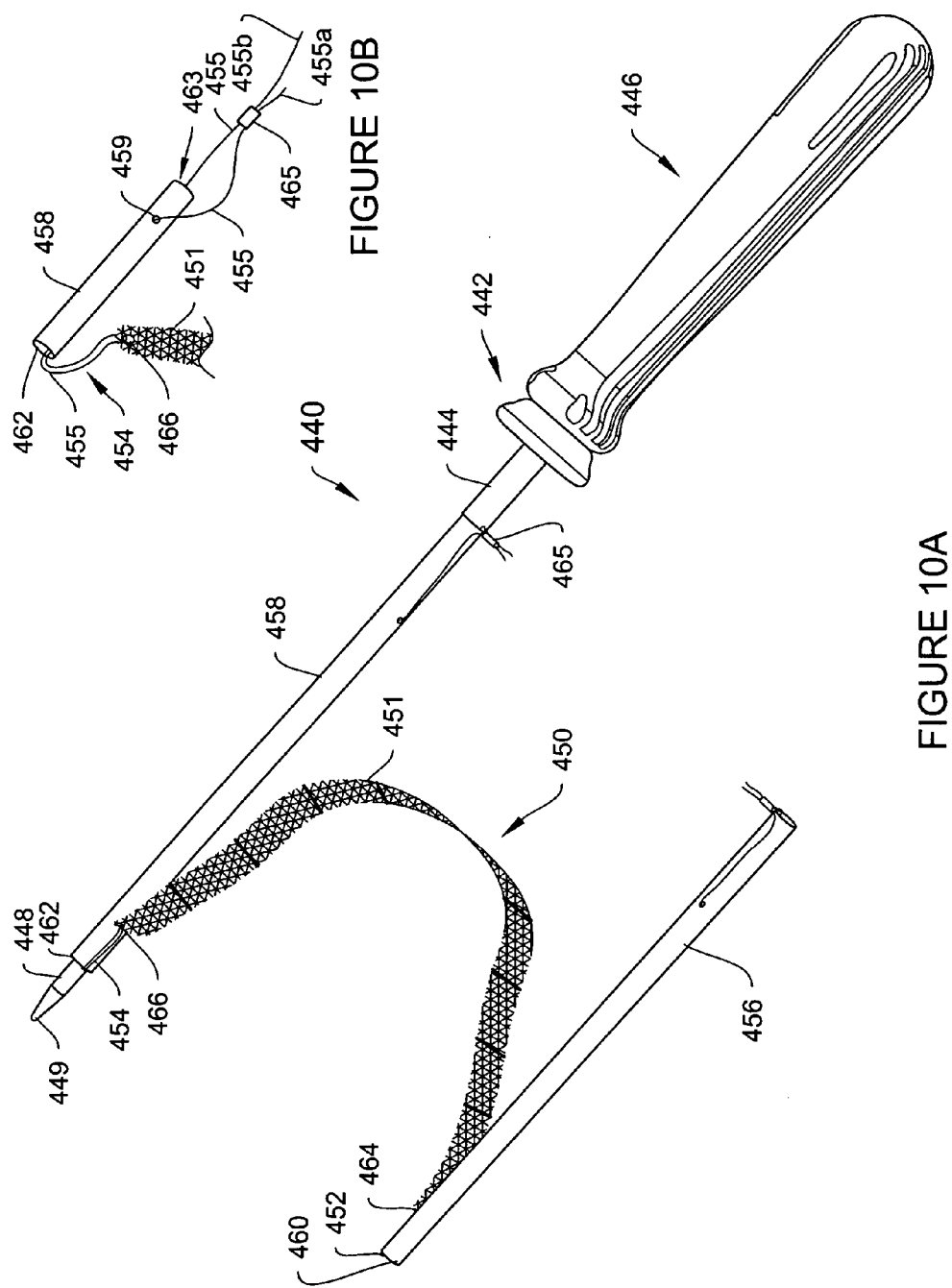
FIGS. 10A and 10B show another illustrative sling delivery system employing a delivery device having a pusher assembly and a sling assembly having extended length association loops threaded through an extended length association tube according to an illustrative embodiment of the invention.

FIG. 10A shows another illustrative sling delivery system 440 employing a delivery device 442 having a pusher assembly 444, a handle 446 and a shaft 448 extending distally from the handle 446. The system 440 also includes a sling assembly 450 having a mesh sling 451 and extended length association loops 452 and 454, each threaded through an extended length association tube 456 and 458, respectively. The delivery device 442 is similar or substantially identical to the delivery device 420 (and may include any of the alternative configurations described with respect to the delivery device 420), except that the pusher assembly 444, preferably, does not extend distally along the shaft 448 as far as the pusher assembly 426 extends along the shaft 424. Preferably, the extended length association tubes 456 and 458 are sized and shaped to expand patient tissue along a tunnel through which the sling 451 passes.

As depicted in FIG. 10B, the association loop 454 is formed from a filament 455. One end (either 455a or 455b) of the filament 455 threads through an opening 464 at one end of the sling assembly 450. The opening 464 may be, for example, a mesh opening or a preformed, structurally reinforced through aperture located at or near an end of the sling assembly 451, and either through a sling included in the sling assembly 451 or through, for example, a protective sleeve enclosing, at least partially, the sling. Both ends 455a and 455b then thread into the extended length association tube 458 at a distal end aperture 462. The ends 455a and 455b then pass axially through the extended length association tube 458 with the end 455a exiting at a side aperture 459 and the end 455b exiting at a proximal end aperture 463. The end 455a threads outside the extended length association tube 458 along a portion of its length. Subsequent to exiting the extended length association tube 456 the ends 455a and 455b are crimped together via the crimping element 465. The association loop 452 threads a substantially identical path with respect to the extended length association tube 456 and the sling end opening 464.

In various configurations, the filament 455 may be formed from any suitable single or multi-stranded material, and in one embodiment is formed from a suturing material.

Additionally, the sling assembly 450 may employ one or two extended length association tubes and/or one or two extended length associate loops. By way of example, a single association tube may be sequentially used for delivering both ends of the sling assembly 451, and thus the entire length, of the sling assembly 451 to an anatomical location in a patient.

In operation, the distal end 449 of the shaft 448 is inserted through either the end 462 or the end 463 (depending on the particular procedure being performed) of the extended length association tube 458 to load the extended length association tube 458 onto the delivery device 442. The distal tip 449 is then inserted into the body of the patient to place one end of the sling 451 at a desired anatomical location. The other end of the sling 451 may be placed in a similar fashion on the contralateral side of the body. Subsequent to verification of desired placement (e.g., via cystoscopy), the medical operator can cut the filament 455 of the association loop 454, for example, near the crimping element 465. The medical operator can then pull on one of the cut ends to de-thread the filament 455 through the extended length association tube 458 and the sling end opening 466 to remove the filament 455 and disengage the extended length association tube 458 from the sling 451. The same procedure may be performed with respect to the extended length association tube 456. According to other illustrative features, the above described methodology may be employed via an initial abdominal incision, ishiopubic incision or transvaginal incision.

In one embodiment, the method includes positioning at least one of first and second ends of a sling included in the sling assembly in front of the pubic bone (i.e., pre-pubicly). In an alternative embodiment, the method includes positioning at least one of the first and second ends of the sling behind the pubic bone (i.e. supra-pubicly). In another embodiment, the method includes positioning at least one of the first and second ends of the sling near the pubic bone. In other embodiments, the method includes positioning at least one of the first and second ends of the sling near or through an obturator foramen (i.e., transobturally).

Figure 11:
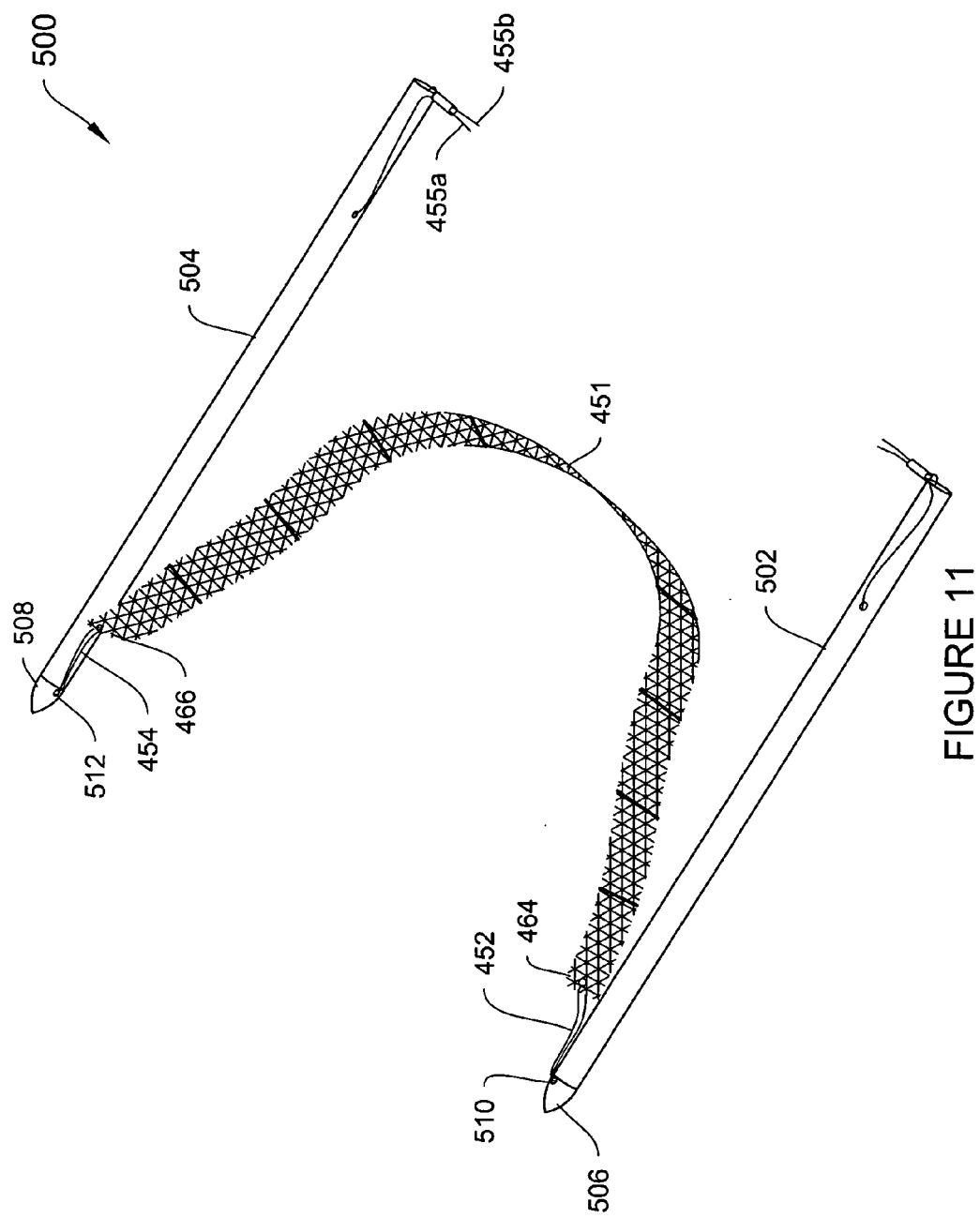
FIG. 11 shows an alternative embodiment of the sling assembly of FIG. 10 in which the extended length association tubes have substantially closed distal ends according to an illustrative embodiment of the invention.

FIG. 11 shows an alternative embodiment of the sling assembly 450 of FIG. 10 in which the extended length association tubes 502 and 504 have substantially closed, conically shaped distal ends 506 and 508, respectively, according to another illustrative embodiment of the invention. In alternative illustrative embodiments, the distal tips 506 and 508 may be pointed or sharp enough to pierce body tissue. Threading of the association loops 452 and 454 is substantially the same as depicted in FIG. 10, except that rather than entering the extended length association tubes 456 and 458 at open ends 460 and 462, respectively, the association loops 506 and 508 of FIG. 11 enter the extended length association tubes 502 and 504 via through apertures 510 and 512, located in the sides of the conical tips 506 and 508, respectively.

According to one advantage of the illustrative embodiment of FIG. 11, the closed conical tips 506 and 508 enable the sling assembly 500 to be employed without the use of a delivery device. Alternatively, the sling assembly 500 may be employed with a delivery device, such as, for example, the delivery device 442 of FIG. 10. Either way, the procedure for sling delivery is substantially the same as described above with respect to FIG. 10.

FIGS. 12A and 12B show another alternative sling delivery system 550 employing a sling assembly 552 of the type depicted in FIGS. 2A and 2B and a delivery device 554 having a shaft 556 extending distally from a handle 560 and including a forked distal tip 558. The distal end 559 includes the forked distal tip 558 which includes a slot 561 that extends axially in a proximal direction from a distal most end 562 of the shaft 556, and is sized and shaped to engage with an opening, loop or other feature in a sling assembly end. The delivery device 554, except for the forked distal tip 558, may include any of the features described above with respect to the delivery devices 252, 420 and 442 of FIGS. 4, 9 and 10A, respectively. A procedure for implanting a sling using the delivery device 554 is substantially the same as the procedures discussed above with respect to the embodiments of FIGS. 4 and 9.

Figure 12:
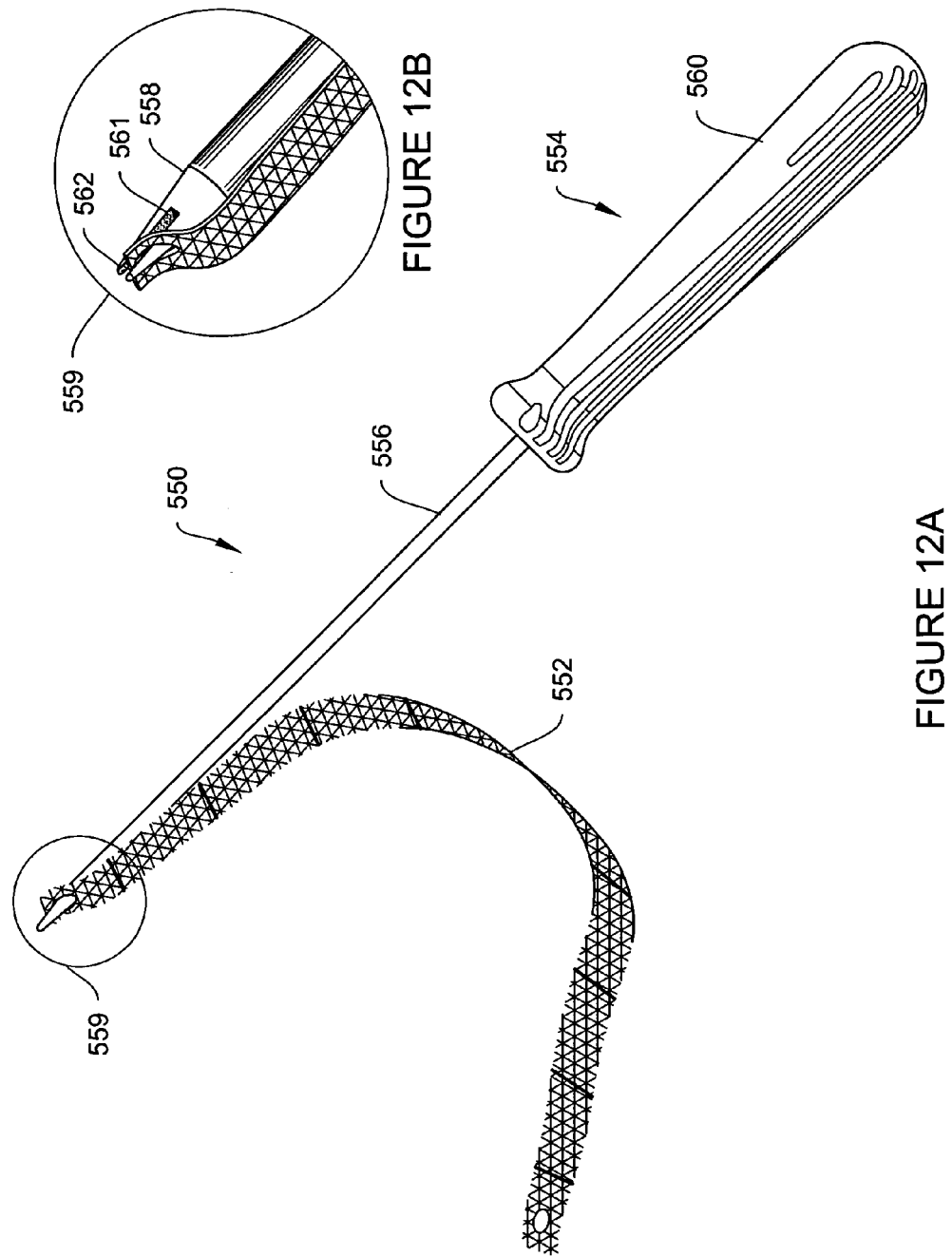
FIGS. 12A and 12B show another alternative sling delivery system employing a sling of the type depicted in FIGS. 2A and 2B and a delivery device having a shaft with a forked distal tip according to an illustrative embodiment of the invention.
Figure 13:
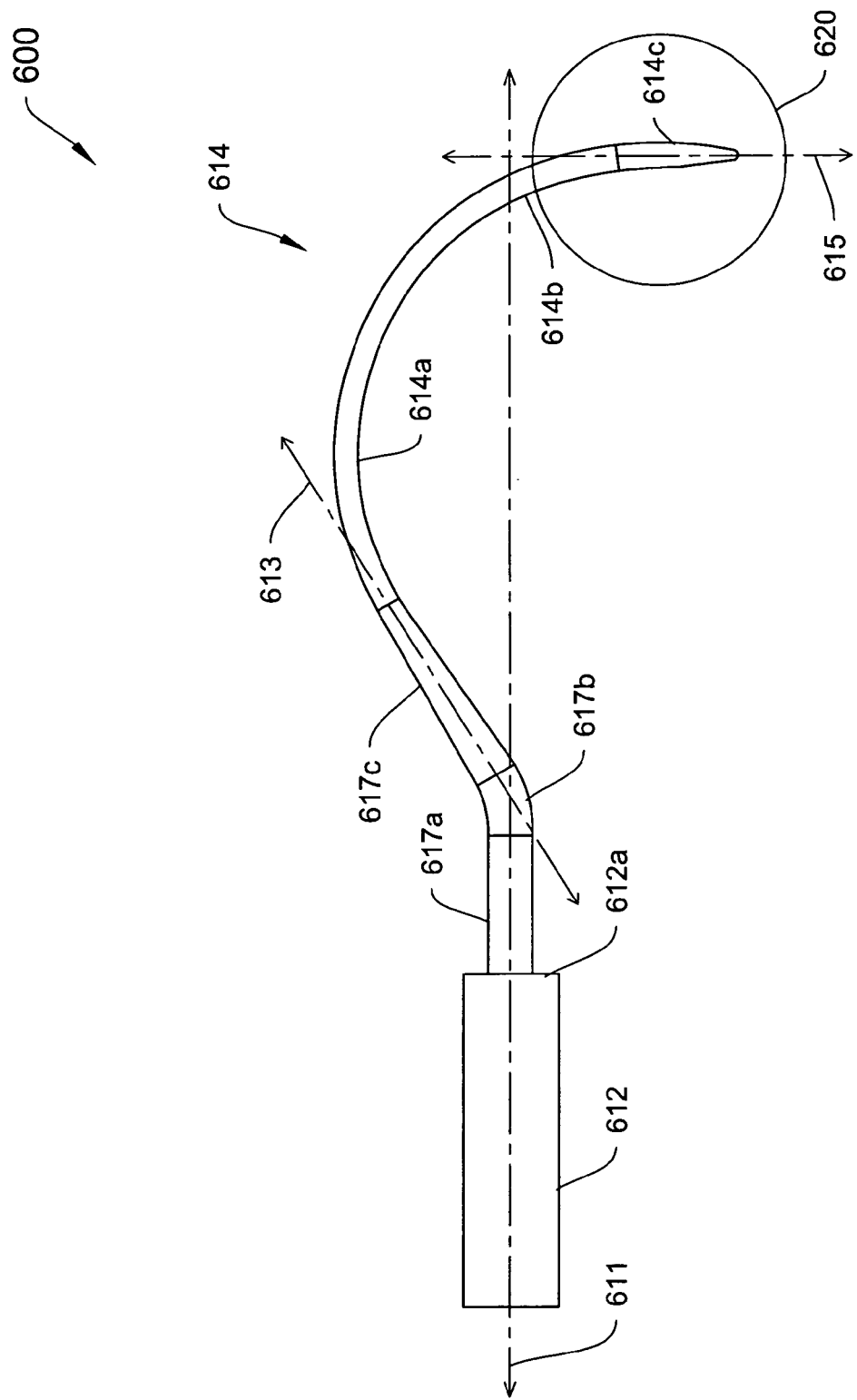
FIG. 13 shows another illustrative delivery device particularly sized and shaped for transobtural placement of an implantable sling, and employable with any of the illustrative embodiments of FIGS. 1A-12B.

FIG. 13 shows another illustrative delivery device 600 particularly sized and shaped for transobtural placement of an implantable sling, and employable with any of the illustrative embodiments of FIGS. 1A-12B. FIG. 13 depicts a side view of the delivery device 600 according to an illustrative embodiment of the invention. The delivery device 600 includes a handle 612, a shaft 614, and a transitional portion 617 extending distally between a distal end 612a of the handle 612 and a proximal end of the shaft 614. The transitional portion 617 includes a first straight section 617a, a curved section 617b and a second straight section 617c, all lying substantially in a single plane, and may be formed as either part of the shaft 614 or as part of the handle 612. The shaft 614 includes a curved section 614a, a straight section 614b and a conical tip 614c, all lying substantially in the same plane as the transitional portion 617. In the illustrative embodiment, the first straight section 617a of the transitional portion 617 attaches to the distal end 612a of the handle 612, extends distally along a first axis 611, and preferably has a substantially constant diameter. The curved section 617b of the transitional portion 617 extends from a distal end of the first straight section 617a, curves away from the first axis 611, and also preferably has a substantially constant diameter. The second straight section 617c extends from a distal end of the curved section 617b along a second axis 613, and preferably has a diameter that decreases from its proximal end to its distal end to provide increased structural stability to the shaft 614. The curved section 614a, preferably, has a substantially constant diameter, smaller than the diameter of the curved section 617b of the transitional portion 617, and extends from the distal end of the second straight section 617c of the transitional portion 617, curves back toward the first axis 611, and terminates at a distal end approximately at an intersection with the first axis 611. The straight section 614b, preferably, has a substantially constant diameter and extends from the distal end of the curved section 614a along a third axis 615, which crosses the first axis 611. In one configuration, a conical tip 614c extends distally from the straight section 614b. In another configuration, the distal end 619 of the delivery device 610 may include a structure or feature for associating the delivery device 610 with a sling and/or sling assembly or an end of a sling and/or sling assembly. A distal portion 620 of the delivery device 610 may include, for example, a structure or feature, such as a forked distal tip as depicted in FIGS. 12A and 12B, a tapered distal portion as depicted in FIG. 1, or a shoulder as depicted in FIG. 3A, for inhibiting an end of a sling and/or sling assembly from sliding proximally along a substantial portion of the length of the delivery device 610. The delivery device of FIG. 13 may be employed with any of the above described sling assemblies, including those of FIGS. 2A, 8, 10A and 11.

Figure 14C:
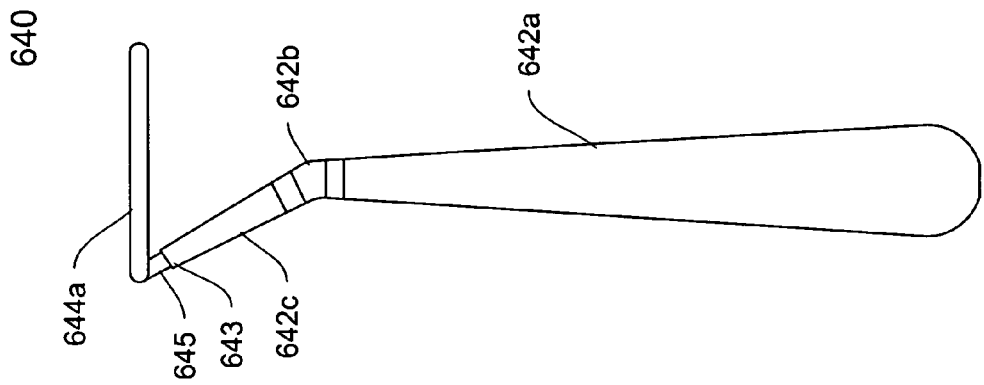
FIGS. 14A-14C show another illustrative delivery device also particularly sized and shaped for transobtural placement of an implantable sling, and employable with any of the illustrative embodiments of FIGS. 1A-12B.
Figure 14B:
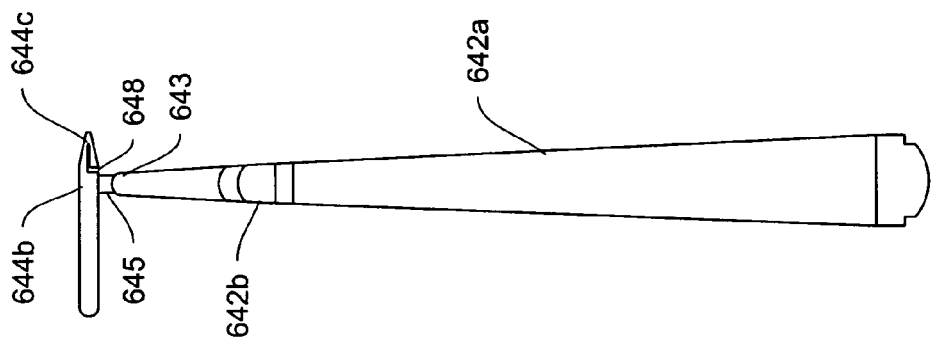
Figure 14A:
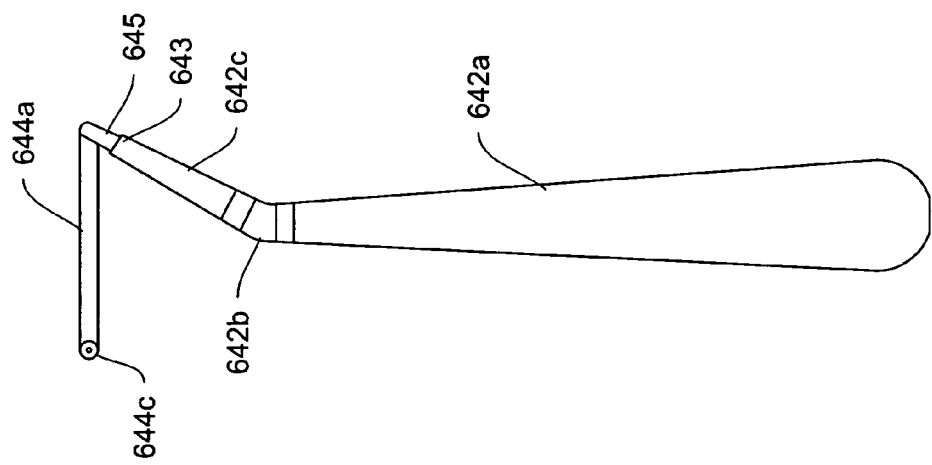

FIGS. 14A and 14B show another illustrative delivery device 640 also particularly sized and shaped for transobtural placement of an implantable sling, and employable with any of the illustrative embodiments of FIGS. 1A-12B. The delivery device 640 includes a handle 642 with first 642a and second 642b substantially straight sections located substantially in a first plane and angled relative to each other, a transitional portion 645 extending out of a distal end 643 of the handle 642, and a shaft 644 extending from a distal end of the transitional portion 645. The shaft includes curved section 644a, a straight section 644b, and in one configuration, terminates in a conical tip 644c. In another configuration, the distal end 649 of the delivery device 640 may include a structure or feature for associating the delivery device 640 with a sling and/or sling assembly or an end of a sling and/or sling assembly. A distal portion 650 of the delivery device 640 may include, for example, a structure or feature, such as a forked distal tip as depicted in FIGS. 12A and 12B, a tapered distal portion as depicted in FIG. 1, or a shoulder as depicted in FIG. 3A, for inhibiting an end of a sling and/or sling assembly from sliding proximally along a substantial portion of the length of the delivery device 640.

The transitional portion 645 interfits and extends axially out of the distal end 643 of the second handle section 642c to affix the shaft 644 to the handle 642. As a result, the transitional portion 645 is substantially co-planer with the handle 642 in the first plane. The curved section 644a of the shaft 644 extends from a distal end of the transitional portion 645. The straight section 644b of the shaft 644 extends from a distal end of the curved section 644a. The curved section 644a and the straight section 644b are substantially coplanar in a second plane. According to the illustrative embodiment of FIGS. 14A and 14B, the first and second plane are substantially orthogonal to each other. However, the first and second planes may be at any suitable angle (e.g., about 10, 20, 30, 45, 60, 70 or 80 degrees) to each other.

To provide structural reinforcement, sections 642b and 642c have a cross sectional diameter that tapers to be smaller at the distal end 643 of the handle 642. Additionally, rather than having the tapered section 617c of the transitional portion 617 being formed as part of the shaft 614, as shown in FIG. 13, the tapered portions 642b and 642c of the embodiment of FIGS. 14A and 14B are formed as part of the handle

642. According to one feature, this configuration reduces the length of the transitional portion 645 and thus, provides improved structural support for the curved section 644*a*. Preferably, in operation, neither the handle 642 nor the intermediate/transitional portion 645 extends into the body of the patient, and provides a positive stop against this occurring. The delivery device of FIGS. 14A-14B may be employed with any of the above described sling assemblies, including those of FIGS. 2A, 8, 10A and 11.

Preferably, the delivery devices and/or delivery assemblies of the invention are made of biocompatible materials, which can include, for example, polyethylene/ethylene vinyl acetate (EVA) blend, polyethylene, polyester, nylon, polypropylene, thermoplastic fluorinated ethylene propylene (FEP), TFP, stainless steel, malleable metal or any combination of these materials. Preferably, a shaft of a delivery device of the invention is formed of surgical grade stainless steel.

One advantage of the above described invention is that it enables a medical operator to place a supportive sling under the bladder neck or the mid-urethra to provide a urethral platform, without requiring any incision other than those made in a vaginal wall. More particularly, employing the devices, systems, methods and features of the invention, a medical operator can place an implantable sling without making any abdominal or ishiopubic incisions. Another advantage is that various embodiments of the invention discussed above can also be employed to place an implantable sling by way of an abdominal or ishiopubic incision. According to other advantages, features of the invention make it easier for a medical operator to disassociate an implantable sling from a remainder of a sling assembly and/or a delivery device.

It should be understood that for the described procedures, and other procedures using the described devices and systems, the delivery devices and sling and/or sling assembly may be tailored, for example, in the dimensions of the devices, such as length, diameter, shape, and curvature, sling assembly, such as length and width of the sling or suture thread, for a particular method of delivery or for placement to a specific anatomical site.

What is claimed is:

1. A method for delivering a sling to an anatomical location in a patient comprising the steps of:
   inserting a delivery device into a body of the patient,
   slidably interfitting a guide element into an axially extending through lumen in the delivery device,
   removing the delivery device from the body of the patient, and
   slidably interfitting over the guide element a dilator tube having a tapered distal portion associated with a first end of a sling assembly for impeding the first end of the sling assembly from sliding proximally along a substantial portion of the dilator tube without impeding the first end of the sling assembly from sliding distally along the distal portion of the dilator tube to deliver the sling included in the sling assembly to the anatomical location.

2. A method for delivering a sling to an anatomical location in a patient including the steps of:
   inserting a dilator tube associated with an end of a sling assembly via an association loop into a body of the patient to deliver an end of the sling to the anatomical location,
   making a single cut in the association loop at a proximal end of the dilator tube,
   pulling on a cut end of the association loop to remove the association loop from the body of the patient and to disassociate the dilator tube from the sling assembly, and
   removing the dilator tube from the body of the patient.

* * * * *